(12) United States Patent
Davidson et al.

(10) Patent No.: US 8,869,797 B2
(45) Date of Patent: Oct. 28, 2014

(54) CUSHION AND CUSHION TO FRAME ASSEMBLY MECHANISM FOR PATIENT INTERFACE

(75) Inventors: Aaron Samuel Davidson, Newport (AU); Robin Garth Hitchcock, Carlingford (AU); Susan Robyn Lynch, Epping (AU); Errol Savio Alex D'Souza, Hornsby (AU); Matthew Eves, Carlingford (AU); David John Worboys, Belrose (AU)

(73) Assignee: ResMed Limited, Bella Vista (AU)

( * ) Notice: Subject to any disclaimer, the term of this patent is extended or adjusted under 35 U.S.C. 154(b) by 1101 days.

(21) Appl. No.: 12/081,696

(22) Filed: Apr. 18, 2008

(65) Prior Publication Data

US 2008/0257354 A1    Oct. 23, 2008

Related U.S. Application Data

(60) Provisional application No. 60/907,856, filed on Apr. 19, 2007, provisional application No. 60/935,336, filed on Aug. 8, 2007.

(51) Int. Cl.
*A62B 18/02* (2006.01)
*A61M 16/06* (2006.01)

(52) U.S. Cl.
CPC ....... *A61M 16/06* (2013.01); *A61M 2016/0661* (2013.01); *A61M 16/0622* (2013.01)
USPC ............ 128/206.24; 128/206.28; 128/206.21; 128/205.25

(58) Field of Classification Search
USPC ............. 128/205.25, 206.21, 206.24–206.26, 128/206.28, 207.13
See application file for complete search history.

(56) References Cited

U.S. PATENT DOCUMENTS

| 443,191 | A | 12/1890 | Illing |
|---|---|---|---|
| 781,516 | A | 1/1905 | Guthrie, Jr. |
| 812,706 | A | 2/1906 | Warbasse |
| 1,081,745 | A | 12/1913 | Johnston |
| 1,125,542 | A | 1/1915 | Humphries |
| 1,192,186 | A | 7/1916 | Greene |
| 1,229,050 | A | 6/1917 | Donald |
| 1,282,527 | A | 10/1918 | Bidonde |

(Continued)

FOREIGN PATENT DOCUMENTS

| AU | 199651130 | 10/1996 |
|---|---|---|
| AU | 2005100738 | 11/2005 |

(Continued)

OTHER PUBLICATIONS

Extended European Search Report, Appln. No. EP 08154854, dated Jul. 30, 2008.

(Continued)

*Primary Examiner* — (Jackie) Tan-Uyen T Ho
*Assistant Examiner* — LaToya M Louis
(74) *Attorney, Agent, or Firm* — Nixon & Vanderhye, P.C.

(57) ABSTRACT

A full-face cushion for a patient interface that delivers breathable gas to a patient includes a frame connector adapted to attach the cushion to a mask frame and an interface provided to the frame connector. The interface is constructed of foam and defines a cushion cavity. The interface includes a foam contact surface adapted to interface or contact with surfaces of the patient's face in use.

17 Claims, 8 Drawing Sheets

(56) References Cited

U.S. PATENT DOCUMENTS

| | | |
|---|---|---|
| 1,362,766 A | 12/1920 | McGargill |
| 1,445,010 A | 2/1923 | Feinberg |
| 1,610,793 A | 12/1926 | Kaufman |
| 1,632,449 A | 6/1927 | McKesson |
| 1,653,572 A | 12/1927 | Jackson |
| 1,710,160 A | 4/1929 | Gibbs |
| 1,926,027 A | 4/1929 | Biggs |
| 1,873,160 A | 8/1932 | Sturtevant |
| 2,011,733 A | 8/1935 | Shindel |
| 2,104,016 A | 1/1938 | Biggs |
| 2,123,353 A | 7/1938 | Catt |
| 2,130,555 A | 9/1938 | Malcom |
| 2,133,699 A | 10/1938 | Heidbrink |
| 2,248,477 A | 7/1941 | Lombard |
| 2,254,854 A | 9/1941 | O'Connell |
| 2,317,608 A | 4/1943 | Heidbrink |
| 2,353,643 A | 7/1944 | Bulbulian |
| 2,371,965 A | 3/1945 | Lehmberg |
| 2,376,871 A | 5/1945 | Fink |
| 2,415,846 A | 2/1947 | Randall |
| 2,428,451 A | 10/1947 | Emerson |
| 2,433,565 A | 12/1947 | Korman |
| 2,438,058 A | 3/1948 | Kincheloe |
| 2,578,621 A | 12/1951 | Yant |
| 2,625,155 A | 1/1953 | Engelder |
| 2,641,253 A | 6/1953 | Engelder |
| 2,706,983 A | 4/1955 | Matheson et al. |
| 2,749,910 A | 6/1956 | Faulconer, Jr. |
| RE24,193 E | 8/1956 | Emerson |
| 2,875,759 A | 3/1959 | Galleher, Jr. |
| 2,881,444 A | 4/1959 | Fresh et al. |
| 2,882,895 A | 4/1959 | Galeazzi |
| 2,902,033 A | 9/1959 | Galleher, Jr. |
| 2,931,356 A | 4/1960 | Schwarz |
| D188,084 S | 5/1960 | Garelick |
| 2,939,458 A | 6/1960 | Lundquist |
| 3,013,556 A | 12/1961 | Galleher |
| 3,182,659 A | 5/1965 | Blount |
| 3,189,027 A | 6/1965 | Bartlett, Jr. |
| 3,238,943 A | 3/1966 | Holley |
| 3,315,674 A | 4/1967 | Bloom et al. |
| 3,330,273 A | 7/1967 | Bennett |
| 3,330,274 A | 7/1967 | Bennett |
| 3,362,420 A | 1/1968 | Blackburn et al. |
| 3,363,833 A | 1/1968 | Laerdal |
| 3,545,436 A | 12/1970 | Holloway |
| 3,556,122 A | 1/1971 | Laerdal |
| 3,580,051 A | 5/1971 | Blevins |
| 3,670,726 A | 6/1972 | Mahon et al. |
| 3,682,171 A | 8/1972 | Dali et al. |
| 3,700,000 A | 10/1972 | Hesse et al. |
| 3,720,235 A | 3/1973 | Schrock |
| 3,739,774 A | 6/1973 | Gregory |
| 3,754,552 A | 8/1973 | King |
| 3,796,216 A | 3/1974 | Schwarz |
| 3,799,164 A | 3/1974 | Rollins |
| D231,803 S | 6/1974 | Huddy |
| 3,861,385 A | 1/1975 | Carden |
| 3,902,486 A | 9/1975 | Guichard |
| 3,905,361 A | 9/1975 | Hewson et al. |
| 3,910,261 A | 10/1975 | Ragsdale et al. |
| 3,938,614 A | 2/1976 | Ahs |
| 3,972,321 A | 8/1976 | Proctor |
| 4,006,744 A | 2/1977 | Steer |
| 4,062,357 A | 12/1977 | Laerdal |
| 4,069,516 A | 1/1978 | Watkins, Jr. |
| 4,077,404 A | 3/1978 | Elam |
| D250,131 S | 10/1978 | Lewis et al. |
| 4,142,527 A | 3/1979 | Garcia |
| 4,153,051 A | 5/1979 | Shippert |
| 4,156,426 A | 5/1979 | Gold |
| 4,167,185 A | 9/1979 | Lewis |
| 4,226,234 A | 10/1980 | Gunderson |
| 4,239,038 A | 12/1980 | Holmes |
| 4,245,632 A | 1/1981 | Houston |
| 4,248,218 A | 2/1981 | Fischer |
| 4,263,908 A | 4/1981 | Mizerak |
| 4,264,743 A | 4/1981 | Maruyama et al. |
| 4,265,239 A | 5/1981 | Fischer, Jr. et al. |
| 4,267,845 A | 5/1981 | Robertson, Jr. et al. |
| 4,273,124 A | 6/1981 | Zimmerman |
| D262,322 S | 12/1981 | Mizerak |
| 4,304,229 A | 12/1981 | Curtin |
| 4,312,359 A | 1/1982 | Olson |
| 4,328,797 A | 5/1982 | Rollins et al. |
| 4,347,205 A | 8/1982 | Stewart |
| 4,354,488 A | 10/1982 | Bartos |
| 4,367,735 A | 1/1983 | Dali |
| 4,367,816 A | 1/1983 | Wilkes |
| 4,402,316 A | 9/1983 | Gadberry |
| 4,406,283 A | 9/1983 | Bir |
| 4,412,537 A | 11/1983 | Tiger |
| 4,414,973 A | 11/1983 | Matheson et al. |
| 4,422,456 A | 12/1983 | Tiep |
| 4,449,526 A | 5/1984 | Elam |
| 4,455,675 A | 6/1984 | Bose et al. |
| 4,467,799 A | 8/1984 | Steinberg |
| 4,493,614 A | 1/1985 | Chu et al. |
| 4,522,639 A | 6/1985 | Ansite et al. |
| 4,548,200 A | 10/1985 | Wapner |
| 4,549,542 A | 10/1985 | Chien |
| 4,558,710 A | 12/1985 | Eichler |
| 4,572,323 A | 2/1986 | Randall |
| 4,587,967 A | 5/1986 | Chu et al. |
| 4,601,465 A | 7/1986 | Roy |
| D285,496 S | 9/1986 | Berman |
| 4,616,647 A | 10/1986 | McCreadie |
| 4,617,637 A | 10/1986 | Chu et al. |
| 4,622,964 A | 11/1986 | Flynn |
| 4,630,604 A | 12/1986 | Montesi |
| 4,641,645 A | 2/1987 | Tayebi |
| 4,641,647 A | 2/1987 | Behan |
| D289,238 S | 4/1987 | Arthur, Jr. |
| 4,655,213 A | 4/1987 | Rapoport et al. |
| 4,660,555 A | 4/1987 | Payton |
| 4,665,570 A | 5/1987 | Davis |
| 4,671,267 A | 6/1987 | Stout |
| 4,671,271 A | 6/1987 | Bishop et al. |
| 4,676,241 A | 6/1987 | Webb et al. |
| 4,677,975 A | 7/1987 | Edgar et al. |
| 4,677,977 A | 7/1987 | Wilcox |
| 4,699,139 A | 10/1987 | Marshall et al. |
| 4,706,664 A | 11/1987 | Snook et al. |
| 4,711,636 A | 12/1987 | Bierman |
| 4,713,844 A | 12/1987 | Westgate |
| H397 H | 1/1988 | Stark |
| D293,613 S | 1/1988 | Wingler |
| 4,739,755 A | 4/1988 | White et al. |
| 4,753,233 A | 6/1988 | Grimes |
| 4,767,411 A | 8/1988 | Edmunds |
| 4,770,169 A | 9/1988 | Schmoegner et al. |
| 4,774,941 A | 10/1988 | Cook |
| 4,774,946 A | 10/1988 | Ackerman et al. |
| 4,782,832 A | 11/1988 | Trimble et al. |
| 4,790,829 A | 12/1988 | Bowden et al. |
| 4,799,477 A | 1/1989 | Lewis |
| 4,802,857 A | 2/1989 | Laughlin |
| 4,803,981 A | 2/1989 | Vickery |
| 4,809,692 A | 3/1989 | Nowacki et al. |
| 4,811,730 A | 3/1989 | Milano |
| 4,819,629 A | 4/1989 | Jonson |
| 4,821,713 A | 4/1989 | Bauman |
| 4,830,138 A | 5/1989 | Palmaer et al. |
| 4,838,878 A | 6/1989 | Kalt et al. |
| 4,841,953 A | 6/1989 | Dodrill |
| 4,848,334 A | 7/1989 | Bellm |
| 4,848,366 A | 7/1989 | Aita et al. |
| 4,899,740 A | 2/1990 | Napolitano |
| 4,905,683 A | 3/1990 | Cronjaeger |
| 4,907,584 A | 3/1990 | McGinnis |
| 4,910,806 A | 3/1990 | Baker et al. |
| 4,914,957 A | 4/1990 | Dougherty |
| 4,915,105 A | 4/1990 | Lee |
| 4,919,128 A | 4/1990 | Kopala et al. |

(56) References Cited

U.S. PATENT DOCUMENTS

| | | |
|---|---|---|
| 4,919,654 A | 4/1990 | Kalt |
| 4,938,210 A | 7/1990 | Shene |
| 4,938,212 A | 7/1990 | Snook et al. |
| 4,941,476 A | 7/1990 | Fisher |
| 4,944,310 A | 7/1990 | Sullivan |
| 4,945,907 A | 8/1990 | Tayebi |
| 4,947,860 A | 8/1990 | Fisher |
| D310,431 S | 9/1990 | Bellm |
| 4,960,121 A | 10/1990 | Nelson et al. |
| 4,966,590 A | 10/1990 | Kalt |
| 4,969,880 A | 11/1990 | Zamierowski |
| 4,971,051 A | 11/1990 | Toffolon |
| 4,976,698 A | 12/1990 | Stokley |
| 4,986,269 A | 1/1991 | Hakkinen |
| 4,989,596 A | 2/1991 | Macris et al. |
| 4,989,599 A | 2/1991 | Carter |
| 4,996,983 A | 3/1991 | Amrhein |
| 5,000,173 A | 3/1991 | Zalkin et al. |
| 5,003,633 A | 4/1991 | Itoh |
| 5,005,568 A | 4/1991 | Loescher et al. |
| 5,005,571 A | 4/1991 | Dietz |
| 5,020,163 A | 6/1991 | Aileo et al. |
| 5,022,900 A | 6/1991 | Bar-Yona et al. |
| 5,023,955 A | 6/1991 | Murphy, II et al. |
| 5,025,805 A | 6/1991 | Nutter |
| 5,038,772 A | 8/1991 | Kolbe et al. |
| 5,038,776 A | 8/1991 | Harrison et al. |
| 5,042,473 A | 8/1991 | Lewis |
| 5,042,478 A | 8/1991 | Kopala et al. |
| 5,046,200 A | 9/1991 | Feder |
| 5,046,491 A | 9/1991 | Derrick |
| 5,062,421 A | 11/1991 | Burns et al. |
| 5,063,922 A | 11/1991 | Hakkinen |
| 5,069,205 A | 12/1991 | Urso |
| 5,074,297 A | 12/1991 | Venegas |
| 5,080,092 A | 1/1992 | Tenna |
| D323,908 S | 2/1992 | Hollister et al. |
| 5,109,839 A | 5/1992 | Blasdell et al. |
| 5,109,840 A | 5/1992 | Daleiden |
| 5,113,857 A | 5/1992 | Dickerman et al. |
| 5,117,818 A | 6/1992 | Palfy |
| 5,121,745 A | 6/1992 | Israel |
| 5,121,746 A | 6/1992 | Sikora |
| 5,127,397 A | 7/1992 | Kohnke |
| 5,133,347 A | 7/1992 | Huennebeck |
| 5,137,017 A | 8/1992 | Salter |
| 5,138,722 A | 8/1992 | Urella et al. |
| 5,140,980 A | 8/1992 | Haughey et al. |
| 5,140,982 A | 8/1992 | Bauman |
| 5,159,938 A | 11/1992 | Laughlin |
| 5,178,138 A | 1/1993 | Walstrom et al. |
| 5,181,506 A | 1/1993 | Tardiff, Jr. et al. |
| D333,015 S | 2/1993 | Farmer et al. |
| 5,188,101 A | 2/1993 | Tumolo |
| D334,633 S | 4/1993 | Rudolph |
| 5,207,665 A | 5/1993 | Davis et al. |
| 5,220,699 A | 6/1993 | Farris |
| 5,222,478 A | 6/1993 | Scarberry et al. |
| 5,231,983 A | 8/1993 | Matson et al. |
| 5,233,978 A | 8/1993 | Callaway |
| 5,243,709 A | 9/1993 | Sheehan et al. |
| 5,243,971 A | 9/1993 | Sullivan |
| 5,245,995 A | 9/1993 | Sullivan et al. |
| 5,261,893 A | 11/1993 | Zamierowski |
| 5,263,939 A | 11/1993 | Wortrich |
| 5,265,592 A | 11/1993 | Beaussant |
| 5,265,595 A | 11/1993 | Rudolph |
| 5,267,557 A | 12/1993 | Her-Mou |
| 5,269,296 A | 12/1993 | Landis |
| 5,271,391 A | 12/1993 | Graves |
| 5,279,289 A | 1/1994 | Kirk |
| 5,280,784 A | 1/1994 | Kohler |
| 5,299,448 A | 4/1994 | Maryyanek |
| 5,299,579 A | 4/1994 | Gedeon et al. |
| 5,299,599 A | 4/1994 | Farmer et al. |
| 5,304,146 A | 4/1994 | Johnson et al. |
| 5,311,862 A | 5/1994 | Blasdell et al. |
| 5,322,057 A | 6/1994 | Raabe et al. |
| D349,586 S | 8/1994 | Handke |
| 5,335,656 A | 8/1994 | Bowe et al. |
| 5,343,878 A | 9/1994 | Scarberry et al. |
| 5,349,949 A | 9/1994 | Schegerin |
| 5,353,789 A | 10/1994 | Schlobohm |
| 5,355,878 A | 10/1994 | Griffiths et al. |
| 5,355,893 A | 10/1994 | Mick et al. |
| 5,357,951 A | 10/1994 | Ratner |
| 5,364,367 A | 11/1994 | Banks et al. |
| 5,372,130 A | 12/1994 | Stem et al. |
| 5,372,388 A | 12/1994 | Gargiulo |
| 5,372,389 A | 12/1994 | Tam et al. |
| 5,372,390 A | 12/1994 | Conway et al. |
| 5,372,391 A | 12/1994 | Bast et al. |
| 5,375,593 A | 12/1994 | Press |
| 5,385,141 A | 1/1995 | Granatiero |
| 5,388,571 A | 2/1995 | Roberts et al. |
| 5,391,248 A | 2/1995 | Brain |
| 5,394,568 A | 3/1995 | Brostrom et al. |
| 5,396,885 A | 3/1995 | Nelson |
| 5,398,676 A | 3/1995 | Press et al. |
| 5,400,776 A | 3/1995 | Bartholomew |
| 5,404,871 A | 4/1995 | Goodman et al. |
| 5,419,318 A | 5/1995 | Tayebi |
| 5,425,359 A | 6/1995 | Liou |
| 5,429,126 A | 7/1995 | Bracken |
| 5,429,683 A | 7/1995 | Le Mitouard |
| 5,431,158 A | 7/1995 | Tirotta |
| 5,437,267 A | 8/1995 | Weinstein et al. |
| 5,438,981 A | 8/1995 | Starr et al. |
| 5,441,046 A | 8/1995 | Starr et al. |
| D362,061 S | 9/1995 | McGinnis et al. |
| 5,462,528 A | 10/1995 | Roewer |
| 5,477,852 A | 12/1995 | Landis et al. |
| 5,479,920 A | 1/1996 | Piper et al. |
| 5,488,948 A | 2/1996 | Dubruille et al. |
| 5,492,116 A | 2/1996 | Scarberry et al. |
| 5,501,214 A | 3/1996 | Sabo |
| 5,503,147 A | 4/1996 | Bertheau |
| 5,509,404 A | 4/1996 | Lloyd et al. |
| 5,509,409 A | 4/1996 | Weatherholt |
| 5,513,634 A | 5/1996 | Jackson |
| 5,513,635 A | 5/1996 | Bedi |
| 5,517,986 A | 5/1996 | Starr et al. |
| 5,526,806 A | 6/1996 | Sansoni |
| 5,533,506 A | 7/1996 | Wood |
| 5,538,000 A | 7/1996 | Rudolph |
| 5,538,001 A | 7/1996 | Bridges |
| 5,540,223 A | 7/1996 | Starr et al. |
| 5,542,128 A | 8/1996 | Lomas |
| 5,546,936 A | 8/1996 | Virag et al. |
| 5,558,090 A | 9/1996 | James |
| RE35,339 E | 10/1996 | Rapoport |
| 5,560,354 A | 10/1996 | Berthon-Jones et al. |
| 5,570,682 A | 11/1996 | Johnson |
| 5,570,684 A | 11/1996 | Behr |
| 5,570,689 A | 11/1996 | Starr et al. |
| D377,089 S | 12/1996 | Starr et al. |
| 5,592,938 A | 1/1997 | Scarberry et al. |
| 5,608,647 A | 3/1997 | Rubsamen et al. |
| 5,623,923 A | 4/1997 | Bertheau et al. |
| 5,642,726 A | 7/1997 | Owens et al. |
| 5,642,730 A | 7/1997 | Baran |
| 5,647,355 A | 7/1997 | Starr et al. |
| 5,647,357 A | 7/1997 | Barnett et al. |
| 5,649,532 A | 7/1997 | Griffiths |
| 5,649,533 A | 7/1997 | Oren |
| 5,653,228 A | 8/1997 | Byrd |
| 5,655,520 A | 8/1997 | Howe et al. |
| 5,655,527 A | 8/1997 | Scarberry et al. |
| 5,657,493 A | 8/1997 | Ferrero et al. |
| 5,657,752 A | 8/1997 | Landis et al. |
| 5,660,171 A | 8/1997 | Kimm et al. |
| 5,662,101 A | 9/1997 | Ogden et al. |
| 5,666,946 A | 9/1997 | Langenback |
| 5,676,133 A | 10/1997 | Hickle et al. |

(56) References Cited

U.S. PATENT DOCUMENTS

| | | |
|---|---|---|
| 5,682,881 A | 11/1997 | Winthrop et al. |
| 5,685,296 A | 11/1997 | Zdrojkowski |
| 5,687,715 A | 11/1997 | Landis et al. |
| D389,238 S | 1/1998 | Kirk, III et al. |
| 5,704,345 A | 1/1998 | Berthon-Jones et al. |
| 5,707,342 A | 1/1998 | Tanaka |
| 5,715,814 A | 2/1998 | Ebers |
| 5,724,965 A | 3/1998 | Handke et al. |
| 5,735,272 A | 4/1998 | Dillon et al. |
| 5,740,799 A | 4/1998 | Nielsen |
| 5,746,201 A | 5/1998 | Kidd |
| 5,752,509 A | 5/1998 | Lachmann et al. |
| 5,752,511 A | 5/1998 | Simmons et al. |
| 5,778,872 A | 7/1998 | Fukunaga et al. |
| 5,782,774 A | 7/1998 | Shmulewitz |
| 5,794,615 A | 8/1998 | Estes |
| 5,794,619 A | 8/1998 | Edeiman et al. |
| 5,807,341 A | 9/1998 | Heim |
| 5,813,423 A | 9/1998 | Kirchgeorg |
| 5,832,918 A | 11/1998 | Pantino |
| 5,842,469 A | 12/1998 | Rapp et al. |
| 5,884,624 A | 3/1999 | Barnett et al. |
| 5,887,587 A | 3/1999 | Groenke |
| 5,906,203 A | 5/1999 | Klockseth et al. |
| 5,918,598 A | 7/1999 | Belfer et al. |
| 5,921,239 A | 7/1999 | McCall et al. |
| D412,745 S | 8/1999 | Scheu |
| 5,935,136 A | 8/1999 | Hulse et al. |
| 5,937,445 A | 8/1999 | Ravo et al. |
| 5,937,851 A | 8/1999 | Serowski et al. |
| 5,954,049 A | 9/1999 | Foley et al. |
| 5,970,975 A | 10/1999 | Estes et al. |
| 5,975,079 A | 11/1999 | Hellings et al. |
| 6,003,511 A | 12/1999 | Fukunaga et al. |
| 6,006,748 A | 12/1999 | Hollis |
| 6,016,804 A | 1/2000 | Gleason et al. |
| 6,019,101 A | 2/2000 | Cotner et al. |
| 6,026,811 A | 2/2000 | Settle |
| 6,039,044 A | 3/2000 | Sullivan |
| 6,044,844 A | 4/2000 | Kwok et al. |
| 6,082,360 A | 7/2000 | Rudolph et al. |
| 6,086,118 A | 7/2000 | McNaughton et al. |
| 6,095,996 A | 8/2000 | Steer et al. |
| 6,098,205 A | 8/2000 | Schwartz et al. |
| 6,102,040 A | 8/2000 | Tayebi et al. |
| 6,109,263 A | 8/2000 | Feuchtgruber |
| 6,112,746 A | 9/2000 | Kwok et al. |
| 6,119,693 A | 9/2000 | Kwok et al. |
| 6,119,694 A | 9/2000 | Correa et al. |
| 6,123,071 A | 9/2000 | Berthon-Jones et al. |
| 6,123,082 A | 9/2000 | Berthon-Jones |
| 6,139,787 A | 10/2000 | Harrison |
| 6,152,137 A | 11/2000 | Schwartz et al. |
| 6,155,253 A | 12/2000 | Gamberini |
| 6,192,886 B1 | 2/2001 | Rudolph |
| 6,193,914 B1 | 2/2001 | Harrison |
| 6,196,223 B1 | 3/2001 | Belfer et al. |
| 6,211,263 B1 | 4/2001 | Cinelli et al. |
| 6,213,125 B1 | 4/2001 | Reese et al. |
| 6,231,548 B1 | 5/2001 | Bassett |
| 6,241,930 B1 | 6/2001 | Harrison |
| 6,258,066 B1 | 7/2001 | Urich |
| 6,295,366 B1 | 9/2001 | Haller et al. |
| 6,328,031 B1 | 12/2001 | Tischer et al. |
| 6,328,038 B1 | 12/2001 | Kessler et al. |
| 6,340,024 B1 | 1/2002 | Brookman et al. |
| 6,341,606 B1 | 1/2002 | Bordewick et al. |
| 6,345,618 B1 | 2/2002 | Hayek |
| 6,347,631 B1 | 2/2002 | Hansen et al. |
| 6,357,440 B1 | 3/2002 | Hansen et al. |
| 6,357,441 B1 | 3/2002 | Kwok et al. |
| 6,358,279 B1 | 3/2002 | Tahi et al. |
| 6,371,110 B1 | 4/2002 | Peterson et al. |
| 6,374,826 B1 | 4/2002 | Gunaratnam et al. |
| 6,397,847 B1 | 6/2002 | Scarberry et al. |
| 6,412,487 B1 | 7/2002 | Gunaratnam et al. |
| 6,412,488 B1 | 7/2002 | Barnett et al. |
| 6,412,593 B1 | 7/2002 | Jones |
| 6,419,660 B1 | 7/2002 | Russo |
| 6,422,238 B1 | 7/2002 | Lithgow |
| 6,423,036 B1 | 7/2002 | Van Huizen |
| 6,425,395 B1 | 7/2002 | Brewer et al. |
| 6,427,694 B1 | 8/2002 | Hecker et al. |
| 6,431,172 B1 | 8/2002 | Bordewick |
| 6,434,796 B1 | 8/2002 | Speirs |
| 6,439,234 B1 | 8/2002 | Curti et al. |
| 6,448,303 B1 | 9/2002 | Paul |
| 6,467,482 B1 | 10/2002 | Boussignac |
| 6,467,483 B1 | 10/2002 | Kopacko et al. |
| 6,470,887 B1 | 10/2002 | Martinez |
| 6,478,026 B1 | 11/2002 | Wood |
| 6,482,178 B1 | 11/2002 | Andrews et al. |
| 6,491,034 B1 | 12/2002 | Gunaratnam et al. |
| 6,513,526 B2 | 2/2003 | Kwok et al. |
| 6,530,373 B1 | 3/2003 | Patron et al. |
| 6,532,961 B1 | 3/2003 | Kwok et al. |
| 6,536,435 B1 | 3/2003 | Fecteau et al. |
| 6,561,188 B1 | 5/2003 | Ellis |
| 6,561,190 B1 | 5/2003 | Kwok et al. |
| 6,561,192 B2 | 5/2003 | Palmer |
| 6,561,193 B1 | 5/2003 | Noble |
| 6,571,798 B1 | 6/2003 | Thornton |
| 6,579,267 B2 | 6/2003 | Lynch et al. |
| 6,581,601 B2 | 6/2003 | Ziaee |
| 6,581,602 B2 | 6/2003 | Kwok et al. |
| 6,584,975 B1 | 7/2003 | Taylor |
| 6,595,214 B1 | 7/2003 | Hecker et al. |
| 6,595,215 B2 | 7/2003 | Wood |
| 6,607,516 B2 | 8/2003 | Cinelli et al. |
| 6,626,177 B1 | 9/2003 | Ziaee |
| 6,627,289 B1 | 9/2003 | Dilnik et al. |
| 6,631,718 B1 | 10/2003 | Lovell |
| 6,634,358 B2 | 10/2003 | Kwok et al. |
| 6,637,434 B2 | 10/2003 | Noble |
| 6,644,315 B2 | 11/2003 | Ziaee |
| 6,651,663 B2 | 11/2003 | Barnett et al. |
| D484,237 S | 12/2003 | Lang et al. |
| 6,655,385 B1 | 12/2003 | Curti et al. |
| 6,663,600 B2 | 12/2003 | Bierman et al. |
| 6,669,712 B1 | 12/2003 | Cardoso |
| D485,905 S | 1/2004 | Moore et al. |
| 6,679,257 B1 | 1/2004 | Robertson et al. |
| 6,679,265 B2 | 1/2004 | Strickland et al. |
| 6,691,708 B2 | 2/2004 | Kwok et al. |
| 6,701,927 B2 | 3/2004 | Kwok et al. |
| 6,710,099 B2 | 3/2004 | Cinelli et al. |
| 6,729,333 B2 | 5/2004 | Barnett et al. |
| 6,766,800 B2 | 7/2004 | Chu et al. |
| 6,766,817 B2 | 7/2004 | da Silva |
| 6,772,760 B2 | 8/2004 | Frater et al. |
| 6,776,162 B2 | 8/2004 | Wood |
| 6,776,163 B2 | 8/2004 | Dougill et al. |
| 6,789,543 B2 | 9/2004 | Cannon |
| 6,796,308 B2 | 9/2004 | Gunaratnam et al. |
| 6,805,117 B1 | 10/2004 | Ho et al. |
| 6,807,967 B2 | 10/2004 | Wood |
| 6,817,362 B2 | 11/2004 | Gelinas et al. |
| 6,820,617 B2 | 11/2004 | Robertson et al. |
| 6,823,865 B2 | 11/2004 | Drew et al. |
| 6,823,869 B2 | 11/2004 | Raje et al. |
| 6,834,650 B1 | 12/2004 | Fini |
| 6,860,269 B2 | 3/2005 | Kwok et al. |
| 6,860,270 B2 | 3/2005 | Sniadach |
| 6,871,649 B2 | 3/2005 | Kwok et al. |
| 6,895,965 B2 | 5/2005 | Scarberry et al. |
| 6,907,882 B2 | 6/2005 | Ging et al. |
| 6,914,091 B2 | 7/2005 | Donald et al. |
| 6,918,404 B2 | 7/2005 | Dias da Silva |
| 6,926,004 B2 | 8/2005 | Schumacher |
| 6,938,620 B2 | 9/2005 | Payne, Jr. |
| 6,959,710 B2 | 11/2005 | Barnett et al. |
| 6,968,844 B2 | 11/2005 | Liland |
| 6,972,003 B2 | 12/2005 | Bierman et al. |
| 6,986,352 B2 | 1/2006 | Frater et al. |

(56) References Cited

U.S. PATENT DOCUMENTS

| | | | |
|---|---|---|---|
| 6,997,177 B2 | 2/2006 | Wood | |
| 7,000,614 B2 | 2/2006 | Lang et al. | |
| 7,007,696 B2 | 3/2006 | Palkon et al. | |
| 7,011,090 B2 | 3/2006 | Drew et al. | |
| 7,018,362 B2 | 3/2006 | Bierman et al. | |
| 7,052,127 B2 | 5/2006 | Harrison | |
| 7,066,586 B2 | 6/2006 | da Silva | |
| 7,076,282 B2 | 7/2006 | Munro et al. | |
| 7,076,822 B2 | 7/2006 | Pearce | |
| 7,080,645 B2 | 7/2006 | Genger et al. | |
| 7,093,599 B2 | 8/2006 | Chen | |
| 7,100,610 B2 | 9/2006 | Biener et al. | |
| 7,101,359 B2 | 9/2006 | Kline et al. | |
| 7,107,989 B2 | 9/2006 | Frater et al. | |
| 7,146,976 B2 | 12/2006 | McKown | |
| 7,152,599 B2 | 12/2006 | Thomas | |
| 7,152,601 B2 | 12/2006 | Barakat et al. | |
| 7,178,525 B2 | 2/2007 | Matula, Jr. et al. | |
| 7,191,781 B2 | 3/2007 | Wood | |
| 7,207,328 B1 | 4/2007 | Altemus | |
| 7,210,481 B1 | 5/2007 | Lovell et al. | |
| 7,237,551 B2 | 7/2007 | Ho et al. | |
| 7,243,723 B2 | 7/2007 | Surjaatmadja | |
| D550,836 S | 9/2007 | Chandran et al. | |
| D552,733 S | 10/2007 | Criscuolo et al. | |
| 7,285,255 B2 | 10/2007 | Kadlec et al. | |
| 7,302,950 B2 | 12/2007 | Berthon-Jones et al. | |
| 7,318,437 B2 | 1/2008 | Gunaratnam et al. | |
| 7,318,439 B2 | 1/2008 | Raje et al. | |
| 7,523,754 B2 | 4/2009 | Lithgow et al. | |
| 7,621,274 B2 | 11/2009 | Sprinkle et al. | |
| 7,631,644 B2 * | 12/2009 | Ho et al. | 128/206.21 |
| 7,658,189 B2 | 2/2010 | Davidson | |
| 7,703,457 B2 | 4/2010 | Barnett et al. | |
| 7,743,767 B2 | 6/2010 | Ging et al. | |
| 7,775,209 B2 | 8/2010 | Biener et al. | |
| 7,779,832 B1 | 8/2010 | Ho | |
| 7,827,990 B1 | 11/2010 | Melidis et al. | |
| 7,856,980 B2 | 12/2010 | Lang et al. | |
| 7,931,024 B2 | 4/2011 | Ho et al. | |
| 7,958,893 B2 | 6/2011 | Lithgow et al. | |
| 7,971,590 B2 | 7/2011 | Frater et al. | |
| 7,997,267 B2 | 8/2011 | Ging et al. | |
| 8,051,850 B2 | 11/2011 | Kwok et al. | |
| 8,091,553 B2 | 1/2012 | Bordewick et al. | |
| 8,136,524 B2 | 3/2012 | Ging et al. | |
| 8,186,352 B2 | 5/2012 | Gunaratnam et al. | |
| 8,210,180 B2 | 7/2012 | Gunaratnam | |
| 8,220,459 B2 * | 7/2012 | Davidson et al. | 128/206.24 |
| 8,485,192 B2 * | 7/2013 | Davidson et al. | 128/206.24 |
| 8,522,784 B2 * | 9/2013 | Ng et al. | 128/206.28 |
| 2001/0020474 A1 | 9/2001 | Hecker et al. | |
| 2002/0005198 A1 | 1/2002 | Kwok et al. | |
| 2002/0020416 A1 | 2/2002 | Namey | |
| 2002/0029780 A1 | 3/2002 | Frater et al. | |
| 2002/0046755 A1 | 4/2002 | Devoss | |
| 2002/0053347 A1 | 5/2002 | Ziaee | |
| 2002/0066452 A1 | 6/2002 | Kessler et al. | |
| 2002/0069872 A1 | 6/2002 | Gradon et al. | |
| 2002/0096178 A1 | 7/2002 | Ziaee | |
| 2002/0124849 A1 | 9/2002 | Billette De Villemeur | |
| 2002/0143296 A1 | 10/2002 | Russo | |
| 2002/0157673 A1 | 10/2002 | Kessler et al. | |
| 2002/0174868 A1 | 11/2002 | Kwok et al. | |
| 2002/0185134 A1 | 12/2002 | Bishop | |
| 2003/0000526 A1 | 1/2003 | Goebel | |
| 2003/0019495 A1 | 1/2003 | Palkon et al. | |
| 2003/0079749 A1 | 5/2003 | Strickland et al. | |
| 2003/0089373 A1 | 5/2003 | Gradon et al. | |
| 2003/0111080 A1 | 6/2003 | Olsen et al. | |
| 2003/0154980 A1 | 8/2003 | Berthon-Jones et al. | |
| 2003/0168063 A1 | 9/2003 | Gambone et al. | |
| 2003/0196656 A1 | 10/2003 | Moore et al. | |
| 2003/0196658 A1 | 10/2003 | Ging et al. | |
| 2004/0025882 A1 | 2/2004 | Madaus et al. | |
| 2004/0025885 A1 | 2/2004 | Payne, Jr. | |
| 2004/0045551 A1 | 3/2004 | Eaton et al. | |
| 2004/0065328 A1 | 4/2004 | Amarasinghe et al. | |
| 2004/0106891 A1 | 6/2004 | Langan et al. | |
| 2004/0111104 A1 | 6/2004 | Schein et al. | |
| 2004/0112384 A1 | 6/2004 | Lithgow et al. | |
| 2004/0112385 A1 | 6/2004 | Drew et al. | |
| 2004/0118406 A1 | 6/2004 | Lithgow et al. | |
| 2004/0127856 A1 | 7/2004 | Johnson | |
| 2004/0182398 A1 | 9/2004 | Sprinkle et al. | |
| 2004/0211428 A1 | 10/2004 | Jones | |
| 2004/0226564 A1 | 11/2004 | Persson | |
| 2004/0226566 A1 | 11/2004 | Gunaratnam et al. | |
| 2005/0005940 A1 * | 1/2005 | Gunaratnam | 128/206.27 |
| 2005/0011523 A1 | 1/2005 | Aylsworth et al. | |
| 2005/0028822 A1 | 2/2005 | Sleeper et al. | |
| 2005/0033247 A1 | 2/2005 | Thompson | |
| 2005/0039757 A1 | 2/2005 | Wood | |
| 2005/0051171 A1 | 3/2005 | Booth | |
| 2005/0051176 A1 | 3/2005 | Riggins | |
| 2005/0056286 A1 | 3/2005 | Huddart et al. | |
| 2005/0061326 A1 | 3/2005 | Payne, Jr. | |
| 2005/0101933 A1 | 5/2005 | Marrs et al. | |
| 2005/0150495 A1 | 7/2005 | Rittner et al. | |
| 2005/0155604 A1 | 7/2005 | Ging et al. | |
| 2005/0211252 A1 | 9/2005 | Lang et al. | |
| 2005/0241644 A1 | 11/2005 | Gunaratnam et al. | |
| 2005/0257792 A1 * | 11/2005 | Wixey et al. | 128/206.24 |
| 2005/0284481 A1 | 12/2005 | Meyer | |
| 2006/0060200 A1 | 3/2006 | Ho et al. | |
| 2006/0081250 A1 | 4/2006 | Bordewick et al. | |
| 2006/0095008 A1 | 5/2006 | Lampropoulos et al. | |
| 2006/0095009 A1 | 5/2006 | Lampropoulos et al. | |
| 2006/0118117 A1 | 6/2006 | Berthon-Jones et al. | |
| 2006/0124131 A1 | 6/2006 | Chandran et al. | |
| 2006/0137690 A1 | 6/2006 | Gunaratnam et al. | |
| 2006/0174887 A1 | 8/2006 | Chandran et al. | |
| 2006/0207597 A1 | 9/2006 | Wright | |
| 2006/0213520 A1 | 9/2006 | Frater et al. | |
| 2006/0237017 A1 | 10/2006 | Davidson et al. | |
| 2006/0283461 A1 | 12/2006 | Lubke et al. | |
| 2007/0023044 A1 | 2/2007 | Kwok et al. | |
| 2007/0125387 A1 | 6/2007 | Zollinger et al. | |
| 2007/0144525 A1 | 6/2007 | Davidson et al. | |
| 2007/0186930 A1 | 8/2007 | Davidson et al. | |
| 2007/0215161 A1 | 9/2007 | Frater et al. | |
| 2007/0272249 A1 | 11/2007 | Chandran et al. | |
| 2007/0282272 A1 | 12/2007 | Bannon et al. | |
| 2008/0004573 A1 | 1/2008 | Kaufmann et al. | |
| 2008/0006277 A1 | 1/2008 | Worboys et al. | |
| 2008/0047560 A1 | 2/2008 | Veliss et al. | |
| 2008/0060649 A1 | 3/2008 | Veliss et al. | |
| 2008/0065022 A1 | 3/2008 | Kyvik et al. | |
| 2008/0110464 A1 * | 5/2008 | Davidson et al. | 128/206.26 |
| 2008/0110469 A1 | 5/2008 | Weinberg | |
| 2008/0200880 A1 | 8/2008 | Kyvik et al. | |
| 2008/0257354 A1 | 10/2008 | Davidson et al. | |
| 2009/0044808 A1 | 2/2009 | Guney et al. | |
| 2009/0078267 A1 * | 3/2009 | Burz et al. | 128/206.24 |
| 2009/0139526 A1 * | 6/2009 | Melidis et al. | 128/206.26 |
| 2009/0173343 A1 | 7/2009 | Omura et al. | |
| 2009/0223518 A1 | 9/2009 | Kwok et al. | |
| 2010/0000534 A1 | 1/2010 | Kooij et al. | |
| 2010/0018534 A1 | 1/2010 | Veliss et al. | |
| 2010/0089401 A1 | 4/2010 | Lang et al. | |
| 2010/0108072 A1 * | 5/2010 | D'Souza et al. | 128/206.24 |
| 2010/0282265 A1 | 11/2010 | Melidis et al. | |
| 2011/0056497 A1 | 3/2011 | Scheiner et al. | |
| 2011/0220110 A1 | 9/2011 | Frater et al. | |
| 2011/0220114 A1 | 9/2011 | Lithgow et al. | |
| 2012/0174928 A1 | 7/2012 | Raje et al. | |

FOREIGN PATENT DOCUMENTS

| | | |
|---|---|---|
| CN | 1735439 | 2/2006 |
| DE | 185017 | 5/1907 |
| DE | 30 11 900 | 10/1980 |
| DE | 146 688 | 2/1981 |
| DE | 31 49 449 | 10/1982 |

(56) References Cited

FOREIGN PATENT DOCUMENTS

| | | |
|---|---|---|
| DE | 37 19 009 | 12/1988 |
| DE | 39 27 038 | 2/1991 |
| DE | 42 33 448 | 4/1993 |
| DE | 196 03 949 | 8/1997 |
| DE | 297 23 101 | 7/1998 |
| DE | 197 03 526 | 8/1998 |
| DE | 199 44 242 | 3/2001 |
| DE | 100 02 571 | 7/2001 |
| DE | 199 62 515 | 7/2001 |
| DE | 102 13 905 | 10/2002 |
| DE | 10 2004 055 433 | 11/2004 |
| DE | 103 31 837 | 1/2005 |
| DE | 20 2004 018 108 | 2/2005 |
| DE | 103 38 169 | 3/2005 |
| EP | 0 288 937 | 11/1988 |
| EP | 0288937 | 11/1988 |
| EP | 0 334 555 | 9/1989 |
| EP | 0 427 474 | 5/1991 |
| EP | 0 466 960 | 1/1992 |
| EP | 0 303 090 | 4/1992 |
| EP | 0 658 356 | 6/1995 |
| EP | 0 747 078 | 12/1996 |
| EP | 0 776 679 | 6/1997 |
| EP | 0 853 962 | 7/1998 |
| EP | 1 099 452 | 5/2001 |
| EP | 1 118 346 | 7/2001 |
| EP | 1 205 205 | 5/2002 |
| EP | 1 258 266 | 11/2002 |
| EP | 1 334 742 | 8/2003 |
| EP | 1 356 841 | 10/2003 |
| EP | 1 360 971 | 11/2003 |
| EP | 1 481 702 | 12/2004 |
| EP | 2 471 566 | 7/2012 |
| EP | 2 471 567 | 7/2012 |
| FR | 2 720 280 | 12/1995 |
| FR | 2 823 122 | 10/2002 |
| GB | 532214 | 1/1941 |
| GB | 649 689 | 1/1951 |
| GB | 2 176 404 | 12/1986 |
| GB | 2 368 533 | 5/2002 |
| GB | 2 385 533 | 8/2003 |
| JP | S51-142793 | 11/1976 |
| JP | H03-007173 | 1/1991 |
| JP | H11-000397 | 1/1999 |
| JP | H11-104256 | 4/1999 |
| JP | 2000-515784 | 11/2000 |
| JP | 2003-175106 | 6/2003 |
| JP | 2003-535657 | 12/2003 |
| JP | 2004-000570 | 1/2004 |
| JP | 2005-337371 | 12/2005 |
| JP | 2005-537906 | 12/2005 |
| JP | 3802872 | 7/2006 |
| WO | WO 82/03548 | 10/1982 |
| WO | WO 87/01950 | 4/1987 |
| WO | WO 92/20392 | 11/1992 |
| WO | WO 92/20395 | 11/1992 |
| WO | WO 96/28207 | 9/1996 |
| WO | WO 98/03145 | 1/1998 |
| WO | WO 98/04310 | 2/1998 |
| WO | WO 98/12965 | 4/1998 |
| WO | WO 98/23305 | 6/1998 |
| WO | WO 98/34665 | 8/1998 |
| WO | WO 98/48878 | 11/1998 |
| WO | WO 99/16327 | 4/1999 |
| WO | WO 99/25410 | 5/1999 |
| WO | WO 99/43375 | 9/1999 |
| WO | WO 99/61088 | 12/1999 |
| WO | WO 00/20072 | 4/2000 |
| WO | WO 00/38772 | 7/2000 |
| WO | WO 00/50121 | 8/2000 |
| WO | WO 00/69521 | 11/2000 |
| WO | WO 00/72905 | 12/2000 |
| WO | WO 00/74758 | 12/2000 |
| WO | WO 00/76568 | 12/2000 |
| WO | WO 00/78384 | 12/2000 |
| WO | WO 01/62326 | 8/2001 |
| WO | WO 01/95965 | 12/2001 |
| WO | WO 01/97892 | 12/2001 |
| WO | WO 01/97893 | 12/2001 |
| WO | WO 02/38221 | 5/2002 |
| WO | WO 02/45784 | 6/2002 |
| WO | WO 03/090827 | 11/2003 |
| WO | WO 03/105921 | 12/2003 |
| WO | WO 2004/007010 | 1/2004 |
| WO | WO 2004/022146 | 3/2004 |
| WO | WO 2004/022147 | 3/2004 |
| WO | WO 2004/041342 | 5/2004 |
| WO | WO 2004/073778 | 9/2004 |
| WO | WO 2004/078230 | 9/2004 |
| WO | WO 2005/018523 | 3/2005 |
| WO | WO 2005/021075 | 3/2005 |
| WO | WO 2005/028010 | 3/2005 |
| WO | WO 2005/053781 | 6/2005 |
| WO | WO 2005/063328 | 7/2005 |
| WO | WO 2005/086943 | 9/2005 |
| WO | 2005/094928 | 10/2005 |
| WO | WO 2005/099801 | 10/2005 |
| WO | WO 2005/110220 | 11/2005 |
| WO | 2005/118040 | 12/2005 |
| WO | 2005/123166 | 12/2005 |
| WO | WO 2005/118040 | 12/2005 |
| WO | PCT/AU2006/000031 | 1/2006 |
| WO | PCT/AU2006/000035 | 1/2006 |
| WO | WO 2006/014630 | 2/2006 |
| WO | PCT/AU2006/000417 | 3/2006 |
| WO | WO 2006/052653 | 5/2006 |
| WO | PCT/AU2006/000770 | 6/2006 |
| WO | WO 2006/069345 | 6/2006 |
| WO | WO 2006/069415 | 7/2006 |
| WO | WO 2006/074513 | 7/2006 |
| WO | WO 2006/074516 | 7/2006 |
| WO | WO 2006/099658 | 9/2006 |
| WO | WO 2006/130903 | 12/2006 |
| WO | WO 2007/009182 | 1/2007 |
| WO | WO 2007/041751 | 4/2007 |
| WO | WO 2007/041786 | 4/2007 |
| WO | WO 2007/048174 | 5/2007 |
| WO | WO 2007/053878 | 5/2007 |
| WO | PCT/AU2007/001936 | 12/2007 |
| WO | WO 2007/143772 | 12/2007 |
| WO | WO 2007/145534 | 12/2007 |
| WO | WO 2008/011682 | 1/2008 |
| WO | WO 2008/011683 | 1/2008 |
| WO | WO 2008/040050 | 4/2008 |
| WO | WO 2008/070929 | 6/2008 |
| WO | WO 2009/108994 | 9/2009 |
| WO | WO 2009/109004 | 9/2009 |
| WO | WO 2010/028425 | 3/2010 |

OTHER PUBLICATIONS

U.S. Appl. No. 60/874,968, filed Dec. 2006, Kwok et al.
U.S. Appl. No. 60/833,841, filed Jul. 2006, Veliss et al.
U.S. Appl. No. 10/385,701, filed Aug. 2003, Berthon-Jones et al.
U.S. Appl. No. 10/533,928, filed Jul. 2005, Berthon-Jones.
U.S. Appl. No. 10/584,711, filed Dec. 2004, Davidson.
U.S. Appl. No. 10/655,622, filed Sep. 2003, Lithgow.
U.S. Appl. No. 10/781,929, filed Jan. 2008, Gunaratnam et al.
U.S. Appl. No. 10/871,929, filed Feb. 2004, Surjaatmadja.
U.S. Appl. No. 11/080,446, filed Jul. 2005, Ging et al.
U.S. Appl. No. 11/447,295, filed Jun. 2006, Lubke et al.
U.S. Appl. No. 11/474,415, filed Jun. 2006, Davidson et al.
U.S. Appl. No. 11/491,016, filed Feb. 2007, Kwok et al.
U.S. Appl. No. 11/597,909, filed Jul. 2007, Worboys.
U.S. Appl. No. 11/703,082, filed Feb. 2007, Davidson.
U.S. Appl. No. 11/878,932, filed Jul. 2007, Veliss et al.
U.S. Appl. No. 11/878,933, filed Jul. 2007, Veliss et al.
U.S. Appl. No. 12/081,696, filed Apr. 2008, Davidson et al.
U.S. Appl. No. 12/085,191, filed May 2008, Kwok et al.
U.S. Appl. No. 12/219,852, filed Jul. 2008, Guney et al.
U.S. Appl. No. 12/382,517, filed Mar. 2009, Lithgow.
U.S. Appl. No. 12/448,250, filed Jun. 2009, Veliss et al.

(56) References Cited

OTHER PUBLICATIONS

U.S. Appl. No. 12/461,448, filed Aug. 2009, Berthon-Jones.
U.S. Appl. No. 12/478,537, filed Jun. 2009, Kooij et al.
U.S. Appl. No. 12/656,466, filed Jan. 2010, Biener et al.
U.S. Appl. No. 12/700,878, filed Feb. 2010, Davidson et al.
U.S. Appl. No. 60/424,686, filed Nov. 2002, Lithgow.
U.S. Appl. No. 60/483,622, filed Jul. 2003, Kwok et al.
U.S. Appl. No. 60/533,214, filed Dec. 2003, Drew.
U.S. Appl. No. 60/634,802, filed Dec. 2004, Chandran.
U.S. Appl. No. 60/645,672, filed Jan. 2005, Chandran.
U.S. Appl. No. 60/795,615, filed Apr. 2006, Judson et al.
U.S. Appl. No. 60/835,442, filed Aug. 2006, Selvarajan et al.
U.S. Appl. No. 60/852,649, filed Oct. 2006, Selvarajan et al.
U.S. Appl. No. 60/924,241, filed May 2007, Kwok et al.
U.S. Appl. No. 60/929,393, filed Jun. 2007, Kwok et al.
U.S. Appl. No. 60/935,179, filed Jul. 2007, Guney et al.
U.S. Appl. No. 60/996,160, filed Nov. 2007, Guney et al.
U.S. Appl. No. 61/006,409, filed Jan. 2008, Guney et al.
U.S. Appl. No. 61/064,818, filed Mar. 2008, Guney et al.
U.S. Appl. No. 61/071,512, filed May 2008, Guney et al.
U.S. Appl. No. 61/213,326, filed May 2009, Dravitzki et al.
U.S. Appl. No. 61/263,175, filed Nov. 2009, Dravitzki et al.
U.S. Appl. No. 61/222,711, filed Jul. 2009, Dravitzki et al.
U.S. Appl. No. 61/272,162, filed Aug. 2009, Dravitzki et al.
U.S. Appl. No. 61/272,250, filed Sep. 2009, Dravitzki et al.
"Ear Loop Face Mask".
Adam J. Singer MD et al. "The Cyanoacrylate Topical Skin Adhesives," American Journal of Emergency Medicine, vol. 26, 2008, pp. 490-496.
Webster's Third New International Dictionary, 1993, Dictionary definition for adjustable, bendable, and mild steel.
ComfortLite™, Respironics, http://comfortlite.respironics.com.
ComfortLite™ 2, Respironics, http://comfortlite2.respironics.com.
"If You Hate CPAP! You Need CPAP Pro®," www.cpappro.com.
Webster's New World Dictionary, Third College Edition 1988, definition for engaged and flexible.
EP Supplementary Search Report issued in EP Application 03793493, dated Dec. 2, 2009.
European Search Report filed on Jul. 27, 2009 in EP Application No. 07784697.0.
European Search Report issued in EP 07845378.4, mailed Dec. 1, 2009.
Examination Report filed in New Zealand Application 539836, dated Aug. 25, 2005.
Examiner's Report No. 3 mailed Nov. 18, 2009 in New Zealand Application No. 2003275762.
Extended European Search Report dated Mar. 19, 2009 in European Application No. EP 08161249.
Extended European Search Report Mailed Sep. 3, 2009 in corresponding EP Application No. 09161984.1.
Fisher and Paykel Col.—Product Family—http://www.fphcare.com/osa/products.asp/.
Hans Rudolph, Inc.—Mask Products—http://www.rudolphhkc.com/products.php?category=MASKS.
International Preliminary Report on Patentability for PCT/AU2004/001832, dated Jul. 3, 2006.
International Search Report for PCT/AU2005/000803, dated Jun. 30, 2005.
International Search Report filed in PCT/AU2006/000770, dated Aug. 3, 2006.
International Search Report for PCT/AU2007/001052, dated Oct. 9, 2007.
International Search Report for PCT/AU2007/001051, dated Nov. 5, 2007.
International Search Report for PCT/AU2004/001832, dated Mar. 24, 2005.
International Search Report for PCT/AU2007/001936, dated Mar. 4, 2008.
Joel W. Beam, "Tissue Adhesives for Simple Traumatic Lacerations," Journal of Athletic Training, 2008, vol. 43, No. 2, pp. 222-224.
Merriam-Webster Online Dictionary definition of moveable from the 14th century.
Office Action mailed Dec. 22, 2009 in European Appln. No. 04802133.1.
ResMed Co.—Mask Products—http://resmed.com/portal/site/ResMedUS/index.jsp? . . . .
Respironics Co.—Mask Family—http://masksfamily.respironics.com/.
Snapp Nasal Interface, Tiara Medical Systems, Inc.—http://www.tiaramed.com/asp_shops/shopdisplayproducts.asp?id=109&cat=SNAPP%2A+Nasal+Interface.
Subbu Venkatraman et al., "Review Skin Adhesives and Skin Adhesion 1. Transdermal Drug Delivery Systems," Biomaterials, vol. 19, 1998, pp. 1119-1136.
Supplementary European Search Report mailed Sep. 8, 2009 in European Appln. No. 04802133.1.
Supplementary Search Report issued in European Appln. 05746824.1, dated Dec. 17, 2009.
Supplementary European Search Report mailed Dec. 18, 2009 in European Application No. 03810331.3.
Unsolicited email from Elson Silva, PhD, dated Mar. 28, 2008, "Requesting IDS of US 6,766,817 for patents on fluids moving on porosity by Unsaturated Hydraulic Flow," (email provided in both HTML and plain text format).
International Search Report PCT/AU2003/001163, dated Nov. 4, 2003.
International Search Report PCT/AU2003/001471, dated Feb. 12, 2004.
International Search Report PCT/AU2009/000240, dated May 21, 2009.
International Search Report PCT/AU2009/000262, dated Jun. 9, 2009.
International Search Report PCT/AU2009/001144, dated Dec. 18, 2009.
Examination Report issued in related European Appln. No. 08154854.7 (Jul. 1, 2011).
U.S. Appl. No. 12/309,696, filed Jan. 2009, Kwok et al.
U.S. Appl. No. 60/833,841, filed Jul. 2006, Veliss.
U.S. Appl. No. 60/907,856, filed Apr. 2007, Davidson et al.
U.S. Appl. No. 60/935,336, filed Aug. 2007, Davidson et al.
Extended European Search Report. Application No. EP 08154854, dated Nov. 27, 2008.
Hans Rudolph, Inc.—Mask Products—http://www.rudolphkc.com/products.php?category=MASKS.
ResMed Co.—Mask Products—http://resmed.com/portal/site/ResMedUS/index.jsp? . . . .
Australian Appln. No. 2005253641—Examiner's First Report, dated Apr. 20, 2010.
Australian Appln. No. 2005253641—Examiner's Report, dated Aug. 18, 2011.
Australian Appln. No. 2006206040—Examination Report, dated Jun. 27, 2012.
Chinese Appln. No. 200580020203.6—Office Action (w/English translation), dated Jun. 1, 2010.
Chinese Appin. No. 200580020203.6—Office Action (w/English translation), dated Jul. 6, 2011.
Chinese Appln. No. 200580020203.6—Office Action (w/English translation), dated Dec. 23, 2011.
Chinese Appln. No. 200580020203.6—Office Action (w/English translation), dated Apr. 18, 2012.
Chinese Appln. No. 200680002169.4—Office Action (w/English translation), dated Mar. 23, 2010.
Chinese Appln. No. 200680002169.4—Third Office Action (w/English translation), dated Nov. 11, 2010.
Chinese Appln. No. 201010000226.3—Office Action (w/English translation), dated Apr. 26, 2012.
European Appln. No. EP 01944732.5—Office Action, dated Nov. 27, 2009.
European Appln. No. EP 03793493.2—Office Action, dated Mar. 18, 2011.
European Appln. No. EP 05749447.8—Supplementary Search Report, dated Dec. 8, 2009.

(56) References Cited

OTHER PUBLICATIONS

European Appln. No. EP 06704287.9—Supplementary Search Report, dated Oct. 6, 2009.
European Appln. No. EP 06704287.9—Office Action, dated Jul. 18, 2011.
European Appln. No. EP 08154854.7—Extended Search Report, dated Nov. 27, 2008.
European Appln .No. EP 09003544.5—Search Report, dated Jun. 2, 2009.
European Appln. No. EP 12154923.2—Extended Search Report, dated Jun. 1, 2012.
European Appln. No. EP 12154926.5—Extended Search Report, dated Jun. 6, 2012.
Japanese Appln. No. 2005-337371—Office Action (w/English translation), dated Feb. 22, 2011.
Japanese Appln. No. 2005-337371—Final Office Action (w/English translation), dated Jan. 31, 2012.
Japanese Appln. No. 2007-515732—Office Action (w/English translation), dated Aug. 24, 2010.
Japanese Appln. No. 2007-515732—Office Action (w/English translation), dated Aug. 16, 2011.
Japanese Appln. No. 2007-515732—Office Action (w/English translation), dated Jun. 12, 2012.
Japanese Appln. No. 2007-550636—Office Action (w/English translation), dated Mar. 18, 2011.
Japanese Appln. No. 2007-550636—Office Action (w/English translation), dated Mar. 21, 2012.
Japanese Appln. No. 2007-550636—Notice of Allowance, dated Jul. 10, 2012.
Japanese Appln. No. 2009-140433—Office Action (w/English translation), dated Aug. 20, 2011.
Japanese Appln. No. 2009-140433—Notice of Allowance, dated Sep. 4, 2012.
Japanese Appln. No. 2010-195597—Office Action (w/English translation), dated Jun. 12, 2012.
Japanese Appln. No. 2010-214485—Office Action (w/English translation), dated Jun. 12, 2012.
Japanese Appln. No. 2011-038110—Office Action (w/English translation), dated Aug. 14, 2012.
JP 11-000397A Machine Translation, provided by the Japanese Patent Office, Jan. 6, 2009, full document.
Laurent Brochard, "Pressure Support Ventilation," Chapter 9, Part IV—Conventional Methods of Ventilator Support, pp. 239-257, 1994.
McPherson et al., "Respiratory Therapy Equipment," Chapter 8, Third Edition, Introduction to Ventilators, pp. 230-253, 1985.
New Zealand Appln. No. 597552—Examination Report, dated Jan. 19, 2012.
New Zealand Appln. No. 587820—Examination Report, dated Sep. 13, 2010.
New Zealand Appln. No. 587344—Examination Report, dated Jan. 19, 2012.
New Zealand Appln. No. 587344—Examination Report, dated Aug. 3, 2012.
PCT/AU2005/000850—International Search Report, dated Aug. 12, 2005.
PCT/AU2005/000850—International Preliminary Report on Patentability, dated Dec. 20, 2006.
PCT/AU2006/000032—International Preliminary Report on Patentability, dated Jul. 17, 2007.
PCT/AU2006/000032—International Search Report, dated May 15, 2006.
PCT/AU2007/001456—International Search Report, dated Dec. 12, 2007.
U.S. Appl. No. 60/643,121, filed Jan. 12, 2005 (expired).
U.S. Appl. No. 60/907,856, filed Apr. 19, 2007 (expired).
U.S. Appl. No. 60/935,336, filed Aug. 8, 2007 (expired).
Office Action issued in related Chinese Appln. No. 200810109270 (Oct. 19, 2011) w/English translation.
European Search Report issued in related EP Appln. No. 11174401.7 (Oct. 20, 2011).
Extended European Search Report issued in related EP Appln. No. 11174407.4 (Oct. 20, 2011).
Office Action issued in a corresponding Chinese Application No. 200810109270.0 (Nov. 13, 2012) with English translation thereof.
Office Action issued in a corresponding Chinese Application No. 200810109270.0 (dated Jun. 27, 2012) with English Translation Thereof.
U.S. Appl. No. 13/537,876, filed Jun. 29, 2012.
Office Action issued in a corresponding Chinese Appln. No. 200810109270.0 (Mar. 28, 2013). with English translation thereof.
Office Action issued in a related Japanese Application No. 2011-185789 (Jan. 15, 2013) with English Translation thereof.
First Office Action issued in related Chinese Patent Application No. 201110339739.1 on Dec. 30, 2013 and English-language translation.
Notification of the Acceptance of a Request for the Invalidation of a Patent Right issued in related Chinese Application No. 200680002169.4 on Nov. 29, 2013, with English-language translation, including the Request for the Invalidation of a Patent Right, citing US 2004/0144386 A1 (Frater et al.) and CN 101862496.
Decision of Rejection issued in related Japanese Patent Application No. 2011-185789 on Oct. 8, 2013 with English-language translation.
Notice of Allowance issued in related Japanese Application No. 2013-084905 on Feb. 17, 2014.
Extended European Search Report issued Feb. 28, 2014 in related European Patent Application No. EP 13 17 8114 listing US 2003/196655, US 2003/145859 and US 2004/221850.
Extended European Search Report issued Mar. 10, 2014 in related European Patent Application No. EP 13 17 8111.
Extended European Search Report issued Mar. 4, 2014 in related European Patent Application No. EP 13 17 8112.
Extended European Search Report issued Mar. 4, 2014 in related European Patent Application No. EP 13 17 8113.
Notice of Opposition issued Jul. 15, 2014 in related European Patent Application No. 2 471 567 with English translation.

\* cited by examiner

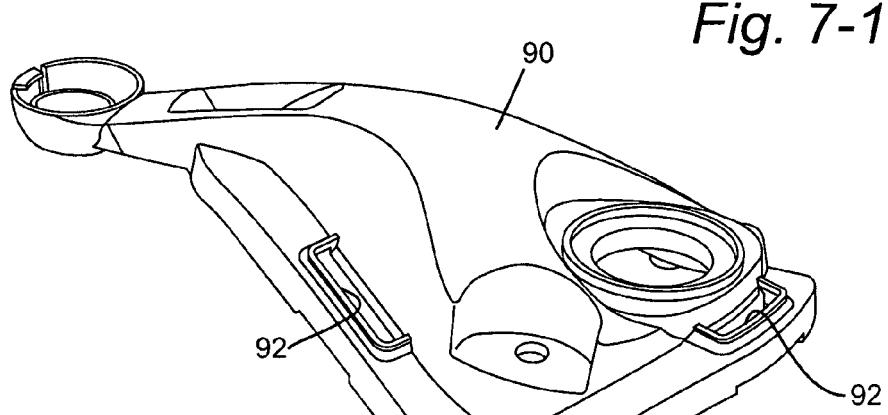
Fig. 7-1
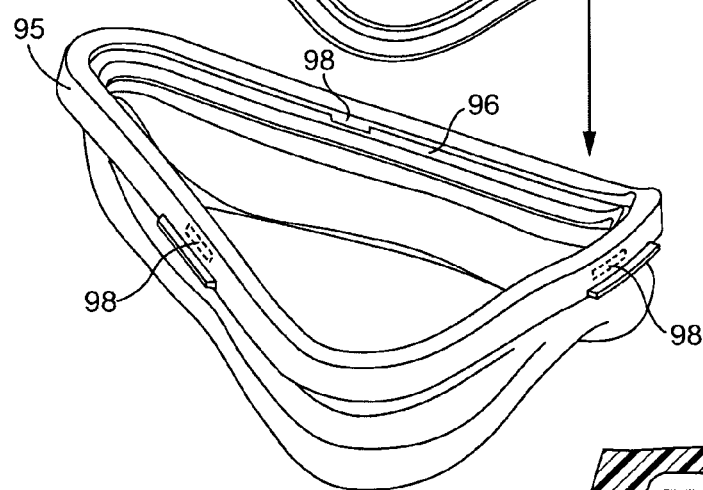
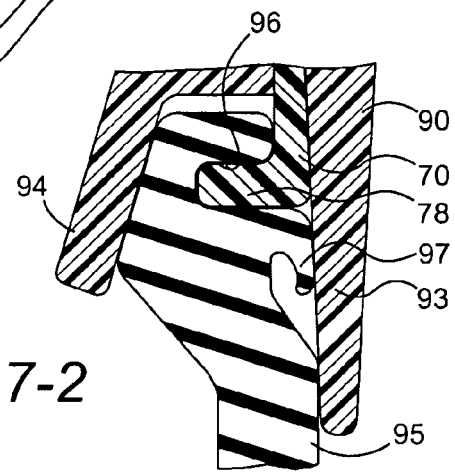
Fig. 7-2

CUSHION AND CUSHION TO FRAME ASSEMBLY MECHANISM FOR PATIENT INTERFACE

CROSS-REFERENCE TO APPLICATIONS

This application claims the benefit of U.S. Provisional Application Nos. 60/935,336, filed Aug. 8, 2007, and 60/907,856, filed Apr. 19, 2007, each of which is incorporated herein by reference in its entirety.

Also, PCT Publication No. WO 2006/074513, published Jul. 20, 2006, and PCT Application No. PCT/AU2006/000035, filed Jan. 12, 2006, are incorporated herein by reference in their entirety.

FIELD OF THE INVENTION

The present invention relates to a cushion for a patient interface used in the treatment, e.g., of Sleep Disordered Breathing (SDB) with Non-Invasive Positive Pressure Ventilation (NPPV). The present invention also relates to a method and apparatus for assembling a cushion to a frame of the patient interface.

BACKGROUND OF THE INVENTION

PCT Publication No. WO 2006/074513 and PCT Application No. PCT/AU2006/000035 describe embodiments of a cushion and a cushion to frame assembly mechanism.

SUMMARY OF THE INVENTION

One aspect of the present invention relates to improvements and/or alternative arrangements of the cushion and cushion to frame assembly mechanism described in PCT Publication No. WO 2006/074513 and PCT Application No. PCT/AU2006/000035 to enhance respiratory therapy.

Another aspect of the invention relates to a full-face cushion for a patient interface that delivers breathable gas to a patient. The full-face cushion includes a frame connector adapted to attach the cushion to a mask frame and an interface provided to the frame connector. The interface is constructed of foam and defines a cushion cavity. The interface includes a foam contact surface adapted to interface or contact with surfaces of the patient's face in use.

Another aspect of the invention relates to a full-face cushion for a patient interface that delivers breathable gas to a patient. The full-face cushion includes a membrane including a uniform wall thickness in the range of 0.15-0.30 mm around the perimeter of the cushion and a foam insert provided to the membrane to support the membrane. The foam insert is structured to provide a variable spring component to the membrane. In alternative embodiments, the thickness of the membrane could be variable from 0.15-0.7 mm, e.g., depending on location around the perimeter of the cushion.

Another aspect of the invention relates to a full-face cushion for a patient interface that delivers breathable gas to a patient. The full-face cushion includes a side wall, a membrane extending away from the side wall and adapted to form a continuous seal on the patient's face in use, and one or more ribs provided to the side wall to vary its spring characteristic.

Another aspect of the invention relates to a full-face cushion for a patient interface that delivers breathable gas to a patient. The full-face cushion includes a frame connector adapted to attach the cushion to a mask frame, a side wall extending away from the frame connector, and a membrane extending away from the side wall and adapted to form a continuous seal on the patient's face in use. The side wall is angled outwardly with respect to the frame connector by an angle to vary the spring characteristic, and the angle may be different in different regions of the cushion.

Another aspect of the invention relates to a full-face cushion for a patient interface that delivers breathable gas to a patient. The full-face cushion includes a membrane including a wall thickness less than 0.3 mm provided in at least a region of the cushion. The thickness may be between about 0.15 mm to 0.30 mm. In alternative embodiments, the thickness of the membrane could be variable from 0.15-0.7 mm, e.g., depending on location around the perimeter of the cushion.

Another aspect of the invention relates to a full-face cushion for a patient interface that delivers breathable gas to a patient. The full-face cushion includes a side wall, an underlying support cushion extending away from the side wall, and a membrane provided to substantially cover at least a portion of the underlying cushion. The underlying support cushion is provided in at least side of nose, upper cheek, lower cheek, and mouth/chin regions of the cushion, and the underlying support cushion in the mouth/chin region has a smaller wall thickness than the other regions.

Another aspect of the invention relates to a full-face mask assembly including a frame, a cushion provided to the frame, and a clip to maintain the cushion to the frame. The cushion is adapted to form a seal around the patient's nose and mouth. The clip includes three clip portions adapted to engage the frame, and the clip includes a flange that extends around the perimeter and three cut-outs are provided in the flange adjacent respective clip portions.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings:

FIG. 1-3 illustrates a foam cushion with different stiffnesses according to an embodiment of the present invention;

FIG. 2-1 illustrates a cushion including a foam insert according to an embodiment of the present invention;

FIG. 3-1 illustrates a cushion including ribs according to an embodiment of the present invention;

FIG. 3-2 illustrates a cushion including ribs according to another embodiment of the present invention;

FIG. 4-1 illustrates a cushion including and angled side wall according to an embodiment of the present invention;

FIGS. 5-1 to 5-3 illustrate a cushion including a very thin membrane wall thickness according to an embodiment of the present invention;

FIGS. 6-1 to 6-6 illustrate a cushion including a thinned undercushion in a mouth/chin region according to an embodiment of the present invention;

FIG. 7-1 illustrates a cushion to frame assembly mechanism according to an embodiment of the present invention; and FIG. 7-2 is a cross-sectional view illustrating the engagement between the cushion clip, cushion, and frame according to an embodiment of the present invention.

DETAILED DESCRIPTION OF ILLUSTRATED EMBODIMENTS

The following description is provided in relation to several embodiments which may share common characteristics and features. It is to be understood that one or more features of any one embodiment may be combinable with one or more features of the other embodiments. In addition, any single feature or combination of features in any of the embodiments may constitute additional embodiments.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

Each illustrated embodiment includes features that may be adapted for use and/or incorporated into the embodiments and/or components of the cushion and/or cushion to frame assembly mechanism described in PCT Publication No. WO 2006/074513 and PCT Application No. PCT/AU2006/000035, as would be apparent to those of ordinary skill in the art. PCT Publication No. WO 2006/074513 and PCT Application No. PCT/AU2006/000035 are each incorporated herein by reference in its entirety.

While each illustrated embodiment is described as being implemented into a cushion and/or cushion to frame assembly mechanism of the type described in PCT Publication No. WO 2006/074513 and PCT Application No. PCT/AU2006/000035, each illustrated embodiment may be implemented into other masks, e.g., full-face mask, mouth mask, nasal mask, nasal prongs, nozzles, nare seals, and/or cannulae.

1. Improvements/Alternative Arrangements

The following embodiments describe improvements and/or alternative arrangements of the cushion and cushion to frame assembly mechanism described in PCT Publication No. WO 2006/074513 and PCT Application No. PCT/AU2006/000035 to enhance respiratory therapy.

2. Variable Spring Characteristic of Cushion

PCT Publication No. WO 2006/074513 discloses a cushion having a varying cross-section around its perimeter to tailor or vary the spring characteristic.

2.1 Foam Cushion to Vary Spring Characteristic

Figure 1:
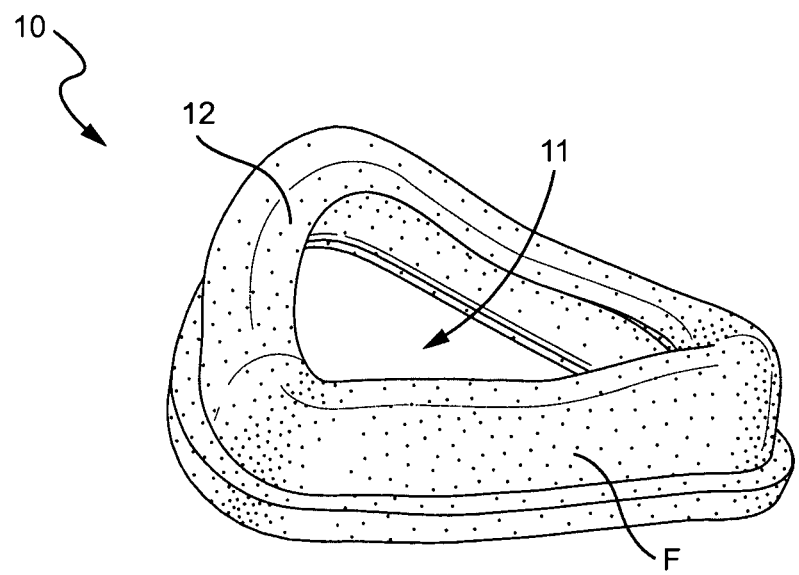
FIGS. 1-1 to 1-2 illustrate a foam cushion according to an embodiment of the present invention.
Figures 1, 2:
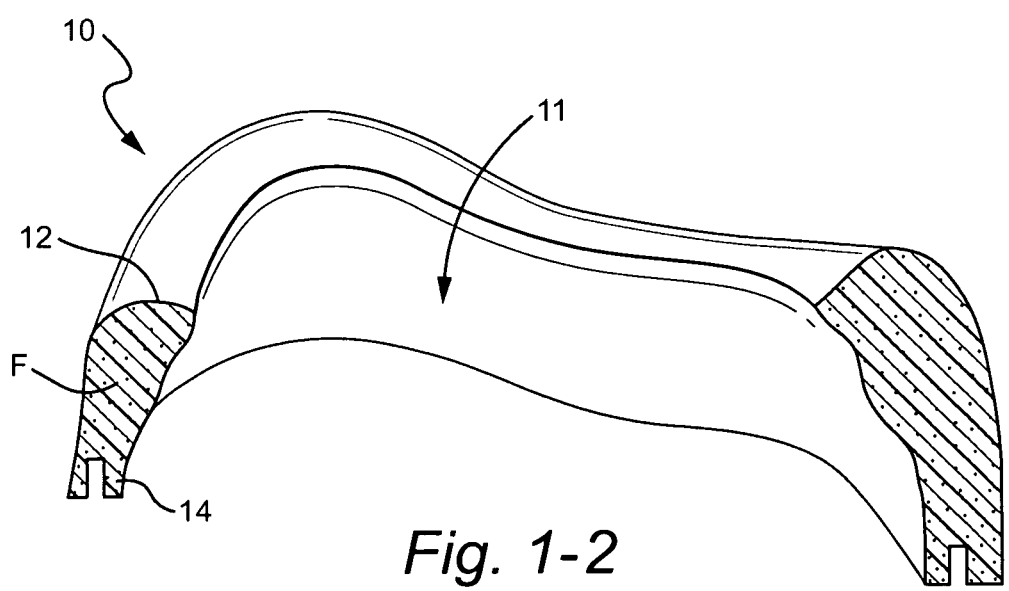

In an alternative embodiment, a cushion may be constructed of a foam material to vary the spring characteristic. For example, FIGS. 1-1 and 1-2 illustrate a foam cushion 10 constructed of a foam material F. As illustrated, the foam cushion 10 provides a foam interface that defines a cushion cavity 11 and includes a foam contact surface 12 adapted to interface or contact with surfaces of the patient's face in use. The foam contact surface 12 may have a similar contour or geometry to that of the cushion illustrated in PCT Publication No. WO 2006/074513. However, the foam contact surface may have other suitable contours or geometries, e.g., to accommodate contours of a particular patient's face.

The foam material F may include one or more of the foam properties described in U.S. Provisional Application No. 60/874,968, filed Dec. 15, 2006, and U.S. Provisional Application No. 60/833,841, filed Jul. 28, 2006, each of which is incorporated herein by reference in its entirety. For example, the foam material may be visco-elastic, de-skinned, etc.

In the illustrated embodiment, the foam cushion 10 includes a frame connector 14 in the form of a grooved portion adapted to attach the cushion to a mask frame. However, the foam cushion 10 may include other suitable frame connectors for attachment to the mask frame, e.g., Velcro®, cushion clip, relatively rigid base, etc.

Figures 1, 2, 3:
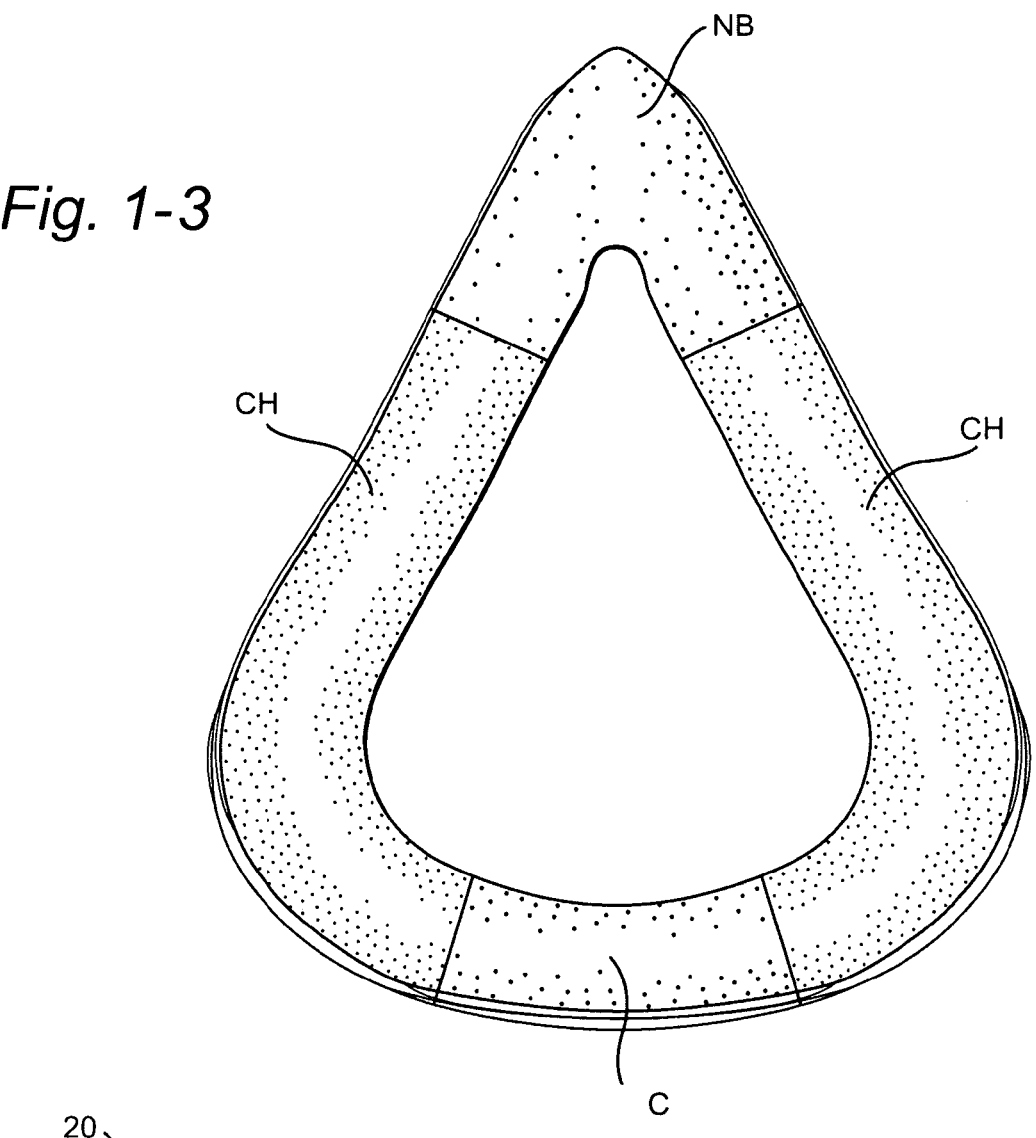
Figures 1, 3:
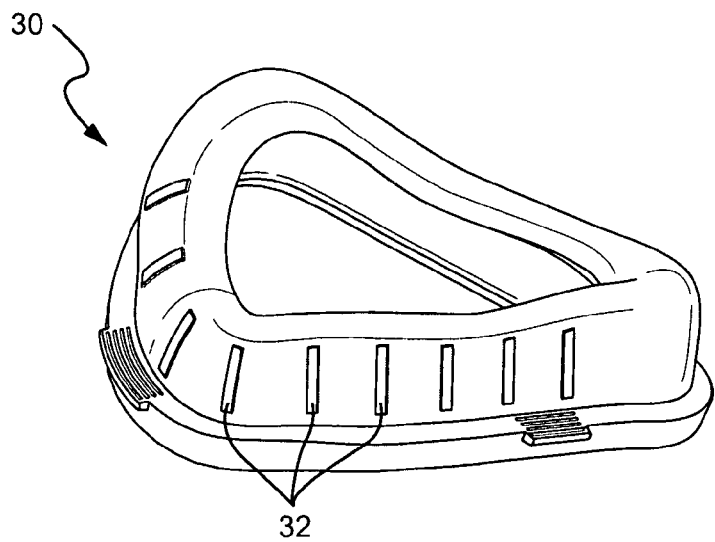
Figures 2, 3:
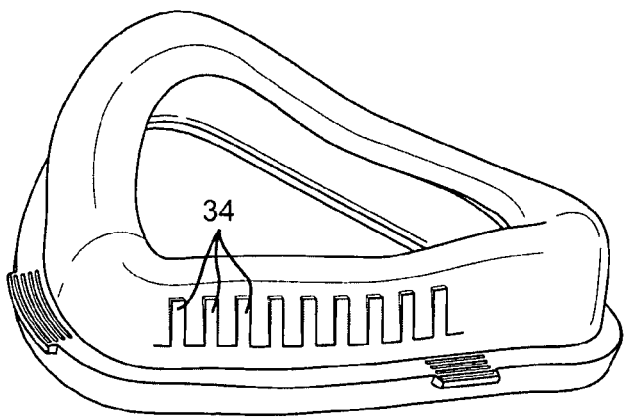

Also, the foam cushion 10 may include different stiffnesses (e.g., by varying the density) in order to vary the spring characteristic. The stiffness of the cushion may be varied in different regions of the cushion, e.g., to tailor the cushion for a particular patient. For example, as shown in FIG. 1-3, the foam cushion may include a relatively softer, less dense foam in nasal bridge and chin regions NB, C, and a relatively harder, more dense foam in cheek regions CH. This arrangement provides higher flexibility in the nasal bridge and chin regions NB, C and lower flexibility in the cheek regions CH, e.g., for stability. However, the foam cushion may have other suitable characteristics around its perimeter.

In an alternative embodiment, foam may be provided in some regions of the cushion and a silicone membrane may be provided in other regions of the cushion. For example, foam may only be used in the cheek region and the silicone membrane may be used in the nasal bridge and chin regions. In this arrangement, support is only provided by the sturdy, less sensitive cheek structures and is less prone to cause an out of balance mask due to protruding or weak chins.

2.2 Foam Insert

In another alternative embodiment, a foam insert may be used in a cushion to vary the spring characteristic. For example, FIG. 2-1 illustrates a cushion 20 including a relatively thin membrane 22 (e.g., of uniform thickness around the entire perimeter (e.g., 0.15-0.3 mm)) and a foam insert 25 provided to the cushion 20 to support the membrane 22 and provide a variable spring component. For example, the membrane may provide a relatively constant or no spring component and the foam insert may provide a variable spring component to vary the spring characteristic of the cushion. In alternative embodiments, the thickness of the membrane could be variable from 0.15-0.7 mm, e.g., depending on location around the perimeter of the cushion.

The foam insert 25 may include one or more of the foam properties described in U.S. Provisional Application No. 60/874,968, filed Dec. 15, 2006, and U.S. Provisional Application No. 60/833,841, filed Jul. 28, 2006, each of which is incorporated herein by reference in its entirety. For example, the foam insert may be visco-elastic, de-skinned, etc.

The foam insert 25 may be retained to the cushion 20 in any suitable manner, e.g., friction-fit, adhesive, mechanical interlock, etc.

Similar to the above, the foam insert 25 may include different stiffnesses (e.g., by varying the density) in order to vary the spring characteristic. The stiffness of the foam insert 25 may be varied in different regions, e.g., to tailor the foam insert for a particular patient.

In an embodiment, the foam insert 25 may be removably mounted or retro-fit to the cushion 20 so that different foam inserts may be used in the cushion from night to night and/or a foam insert may be optionally used in the cushion, e.g., foam insert used on alternate nights.

Also, in an alternative embodiment, a foam insert may only be provided in selected regions of the cushion in order to vary the spring characteristic in the selected region. For example, a foam insert may only be used in the cheek region which provides a sturdy, less sensitive support.

In another embodiment, the base of the foam insert may be angled in selected regions so that compression of the foam insert is normal or perpendicular to facial structures, e.g., base of the foam insert angled to align the membrane to be perpendicular to the sides of the patient's nose.

2.3 Cushion with Ribs

In another alternative embodiment, a cushion may be provided with one or more ribs to vary the spring characteristic. For example, FIG. 3-1 illustrates a cushion 30 including a series of ribs 32 that extend around the perimeter of the cushion. The ribs 32 may be integrally formed with the cushion and/or attached to the cushion, e.g., by an adhesive.

In the illustrated embodiment, the series of ribs 32 are provided to an external surface of the cushion, e.g., along an external surface of the cushion side wall. However, the ribs may be provided to other suitable portions of the cushion, e.g., along an internal surface of the cushion side wall.

Also, each rib 32 includes an elongated configuration and extends vertically along the cushion side wall in spaced apart relation from the other ribs. However, the ribs may have other suitable configurations and arrangements to vary the spring characteristic, e.g., different shape, length, width, thickness, spacing around perimeter, orientation, etc. For example, FIG. 3-2 illustrates a cushion including a series of interconnected ribs 34.

In addition, the rib configuration and/or arrangement may be varied in different regions of the cushion, e.g., to tailor the stiffness of the cushion for a particular patient. For example, the cushion may include no ribs in nasal bridge and chin regions to allow higher flexibility in these regions, and the cushion may include a series of ribs in cheek regions to allow lower flexibility in these regions, e.g., for stability. However, the rib configuration and/or arrangement may be varied in other suitable manners around the cushion perimeter.

In an embodiment, the ribs may replace an underlying support cushion or undercushion to vary the spring characteristic. In another embodiment, the ribs may be used in conjunction with an undercushion to vary the spring characteristic.

2.4 Angled Cushion Shape

Figures 1, 4:
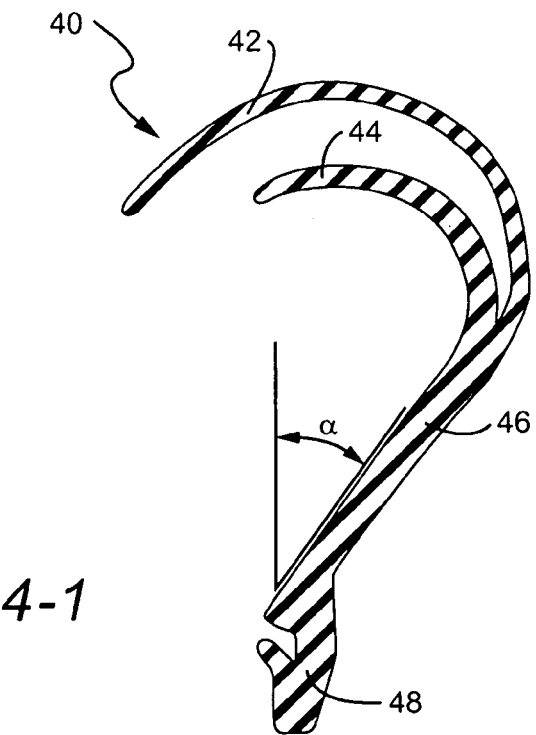

PCT Publication No. WO 2006/074513 discloses a cushion wherein one or more portions have a sickle-shaped cross-sectional configuration. In an alternative embodiment, the cushion may have one or more portions with an angled-shaped cross-sectional configuration to vary the spring characteristic. For example, FIG. 4-1 illustrates a cushion 40 including a membrane 42, an optional underlying support cushion or undercushion 44, a base or side wall 46, and a frame connector 48 adapted to attach the cushion to a mask frame.

In the illustrated embodiment, the side wall 46 is angled outwardly with respect to the frame connector 48 by an angle α. The angle α may be varied to vary the spring characteristic provided by such angled side wall. However, other cushion parameters may be varied to vary the spring characteristic, e.g., wall thickness, length, undercushion radius, etc.

In addition, the angle a and/or other cushion parameters may be varied in different regions of the cushion, e.g., to tailor the stiffness of the cushion for a particular patient. For example, the angle α may be varied to allow higher flexibility in more sensitive regions, e.g., nasal bridge region, and lower flexibility in less sensitive regions, e.g., cheek region. However, the angle α and/or other cushion parameters may be varied in other suitable manners around the cushion perimeter.

3. Nasal Bridge Region of Cushion

PCT Publication No. WO 2006/074513 discloses a cushion having a membrane with a relatively thin wall thickness in the nasal bridge region, e.g., 0.3 mm thick.

3.1 Very Thin Membrane Wall Thickness

Figures 1, 5:
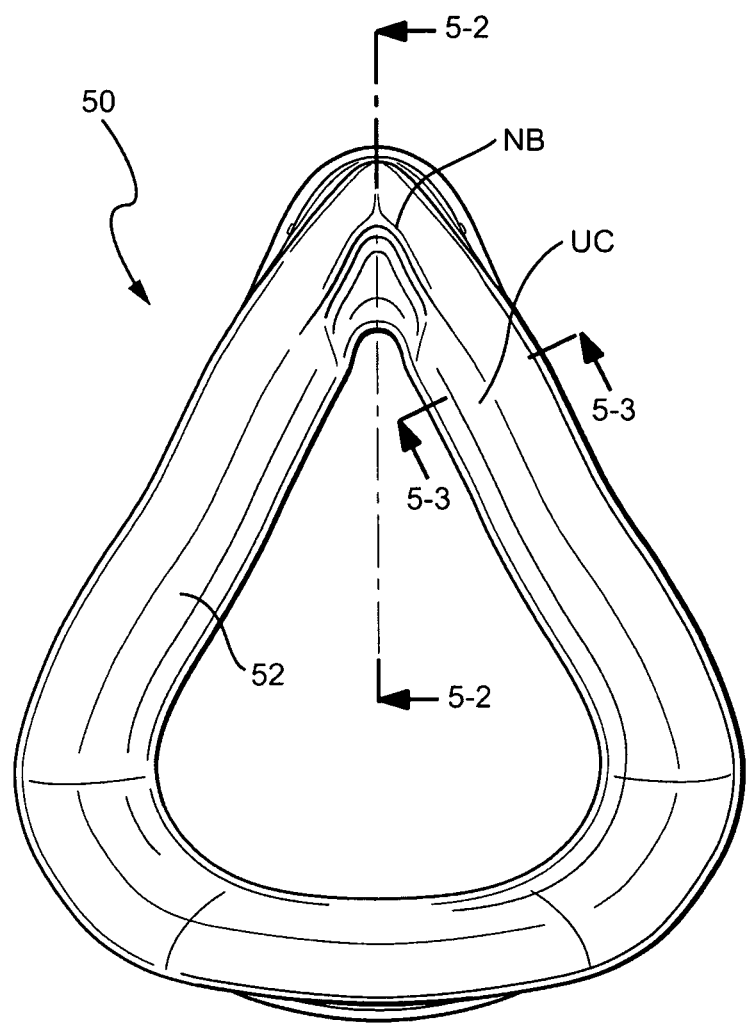
Figures 2, 5:
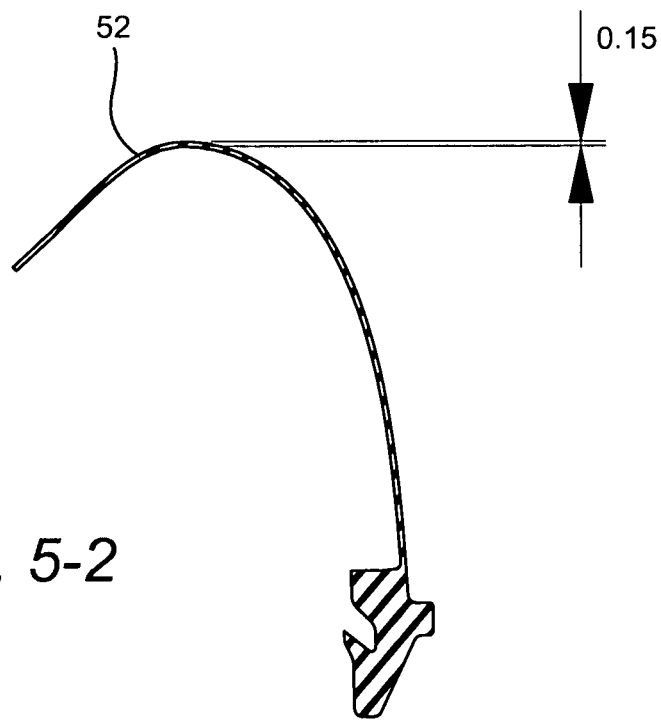
Figures 3, 5:
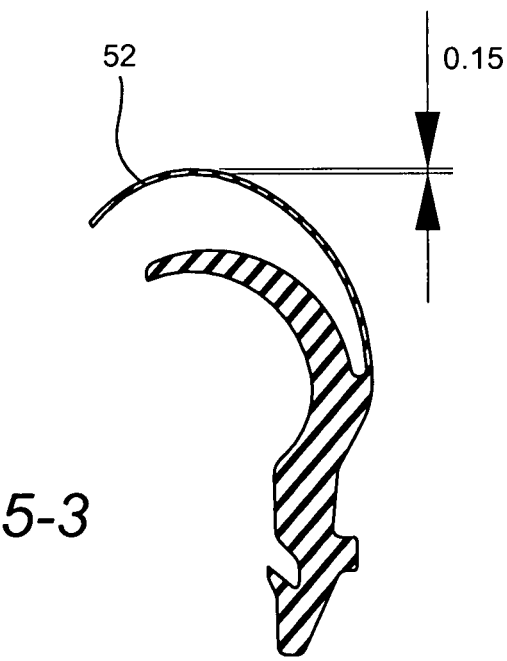

In an alternative embodiment, one or more regions of a cushion may have a membrane with a wall thickness less than 0.3 mm thick. For example, FIGS. 5-1 to 5-3 illustrate a cushion 50 having a membrane 52 with a wall thickness of about 0.15 mm. As illustrated, such 0.15 mm membrane wall thickness is provided in a nasal bridge region NB and a side of nose and/or upper cheek region UC of the cushion. Other regions of the cushion, e.g., lower cheek and chin regions, may have thicker membrane wall thicknesses, e.g., 0.5 mm. This arrangement provides higher flexibility in more sensitive regions, e.g., nasal bridge and upper cheek regions, and lower flexibility in less sensitive regions, e.g., cheek and chin regions. However, the wall thickness of the membrane may be varied in other suitable manners around the cushion perimeter. In alternative embodiments, the thickness of the membrane could be variable from 0.15-0.7 mm, e.g., depending on location around the perimeter of the cushion.

4. Mouth/Chin Region of Cushion

PCT Publication No. WO 2006/074513 discloses a cushion that includes a cut-out of the undercushion in the mouth/chin region.

4.1 Thinned Section for Undercushion

Figures 1, 6:
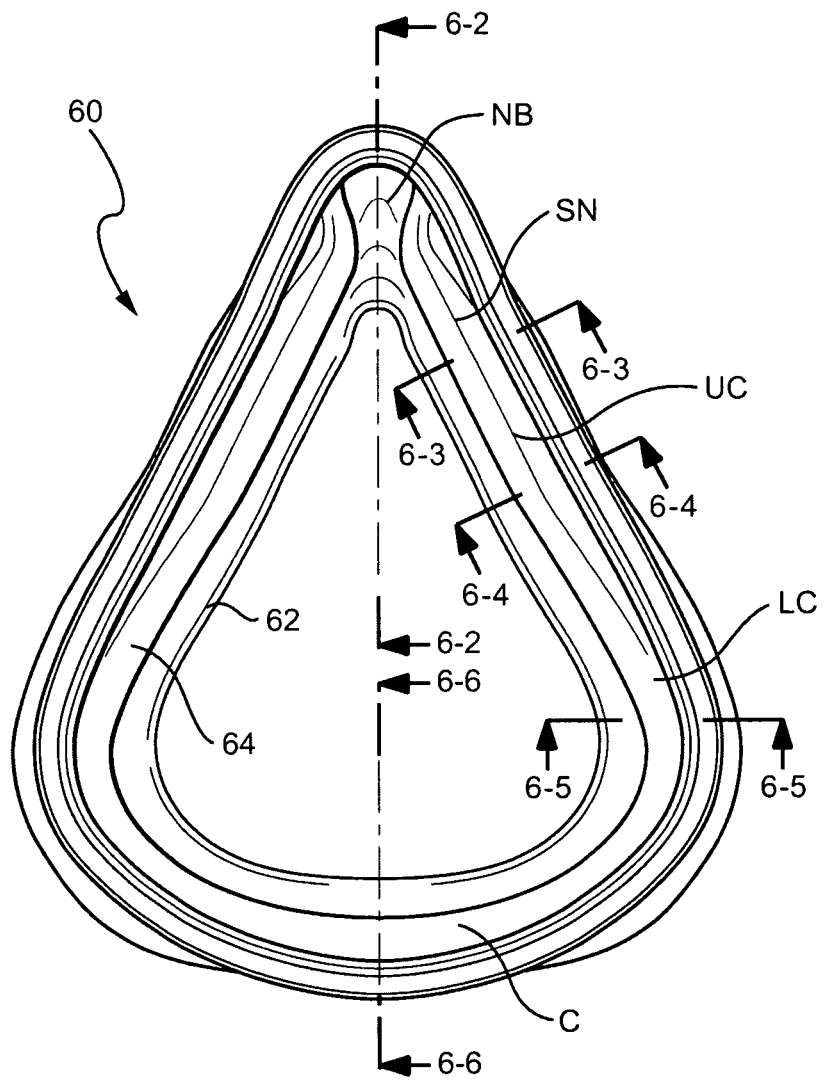
Figures 2, 6:
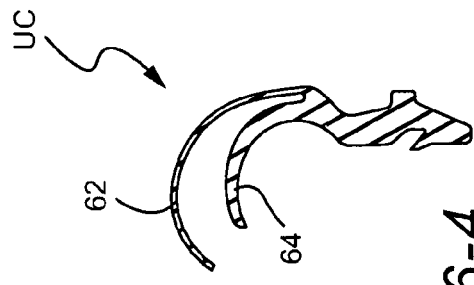
Figures 3, 6:
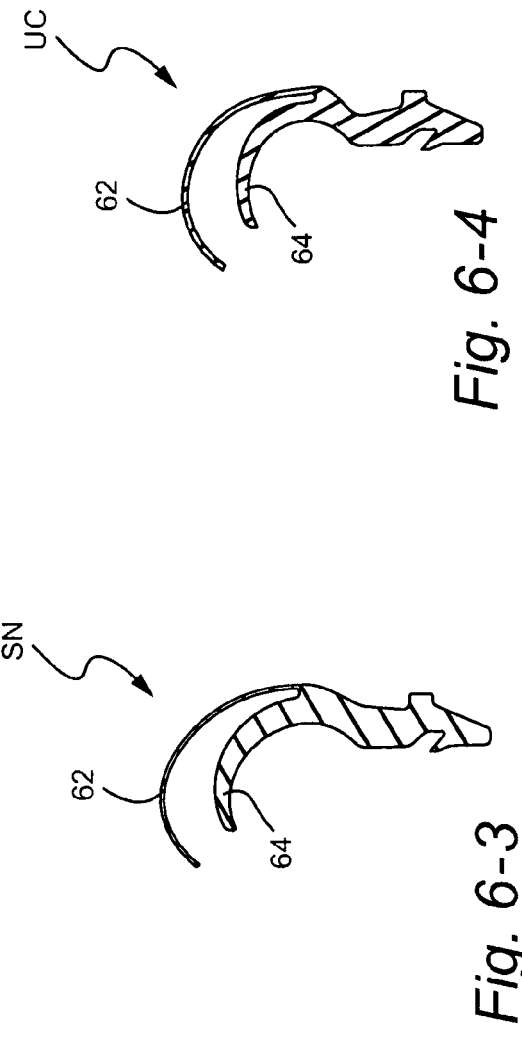
Figures 4, 6:
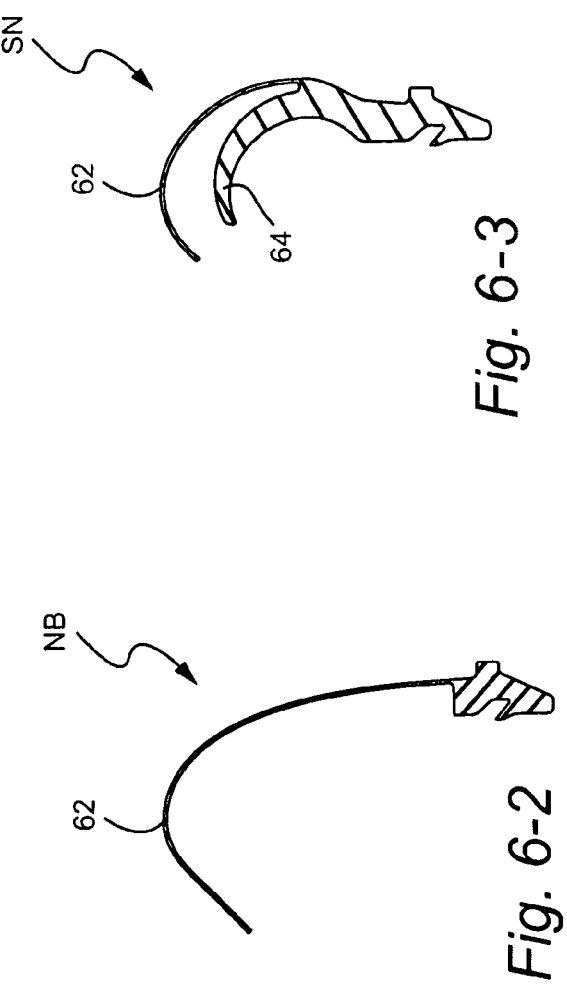
Figures 5, 6:
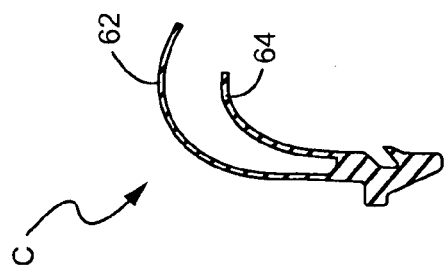
Figure 6:
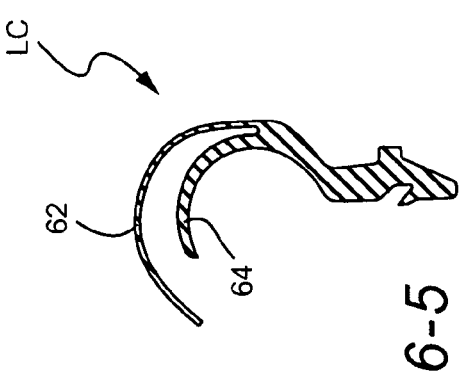

In an alternative embodiment, the mouth/chin region of the cushion may include an undercushion. For example, FIGS. 6-1 to 6-6 illustrate a cushion 60 including a membrane 62 and an underlying support cushion or undercushion 64 provided to side of nose region SN, upper cheek region UC, lower cheek region LC, and mouth/chin region C of the cushion. Although an undercushion is not illustrated in the nasal bridge region NB (e.g., see FIG. 6-2), the cushion may include an undercushion in the nasal bridge region NB in an alternative embodiment, e.g., undercushion extends around entire perimeter of the cushion.

In the illustrated embodiment, the wall thickness of the undercushion in the mouth/chin region C may be thinner than the undercushion in other regions of the cushion. For example, as shown in FIGS. 6-3 to 6-6, the wall thicknesses of the undercushion 64 in the side of nose region SN, upper cheek region UC, and lower cheek region LC are thicker than the undercushion 64 in the mouth/chin region C. This arrangement provides higher flexibility in the mouth/chin region C, which may be more sensitive. However, the wall thickness of the undercushion may be varied in other suitable manners around the cushion perimeter.

4.2 Series of Ribs

In another alternative embodiment, the undercushion may be replaced with a series of ribs that extend around the perimeter of the cushion, e.g., ribs of varying thickness and/or width to vary the spring characteristic. Further details and arrangements of such ribs are described above in section 2.3.

5. Cushion to Frame Assembly Mechanism

PCT Application No. PCT/AU2006/000035 discloses a mask assembly including an internal-style cushion clip with three attachment points to removably connect a cushion to a mask frame.

5.1 Cushion to Cushion Clip Attachment

In an embodiment, the mask assembly may include a cushion clip with three cut-outs that are adapted to interlock with respective solid sections provided in the retaining recess of the cushion.

For example, FIG. 7-1 illustrates a cushion clip 70 including side clip portions 72, 74 and a bottom clip portion 76 adapted to engage respective slots 92 provided on the frame 90 (one of the slots hidden in FIG. 7-1). It should be appreciated that the cushion clip 70 may have any suitable number of clip portions, and the number of slots in the frame 90 may be varied according to the number of clip portions. Also, the cushion clip 70 includes a flange 78 around the perimeter, and slots or cut-outs 80 are provided in the flange 78 adjacent respective clip portions 72, 74, 76.

In use, the cushion clip 70 is first assembled or interlocked with the cushion 95 to provide a cushion clip/cushion sub-assembly, and then the cushion clip/cushion sub-assembly is engaged with the frame 90 by inserting the clip portions 72, 74, 76 of the cushion clip 70 into respective slots 92 of the frame 90, e.g., with a snap-fit.

The cushion clip 70 is assembled to the cushion 95 by engaging the flange 78 of the cushion clip 70 within the retaining recess 96 of the cushion 95. The cut-outs 80 in the cushion clip 70 are adapted to interlock or engage with respective solid sections 98 provided in the retaining recess, i.e., solid sections provided on opposing sides and the bottom of the cushion. The three cut-outs/solid sections assist with correct orientation or alignment of the cushion clip 70 onto the cushion 95. However, other suitable numbers of cut-outs/solid sections may be provided.

FIG. 7-2 is an exemplary cross-sectional view illustrating the engagement between the cushion clip 70, cushion 95, and frame 90. As illustrated, the cushion 95 is sandwiched between inner and outer walls 93, 94 of the frame 90 and the cushion 95 may include a lip seal 97 adapted engage the inner wall 93 and provide a seal.

In the illustrated embodiment, the side clip portions 72, 74 include a different structure or configuration than the bottom clip portion 76. As illustrated, the side clip portions 72, 74 are relatively thick and include contoured finger grips 82 to facilitate assembly. The bottom clip portion 76 has a lower profile than the side clip portions 72, 74 and does not provide finger grips. However, the clip portions 72, 74, 76 may have other suitable arrangements, e.g., bottom clip portion similar structure to side clip portions.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. Furthermore, each individual component of any given assembly, one or more portions of an individual component of any given assembly, and various combinations of components from one or more embodiments may include one or more ornamental design features. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. A full-face cushion for a patient interface that delivers breathable gas to a patient, the cushion comprising different regions including nasal bridge, cheek and chin regions, the cushion being adapted to be connected to a frame, the full-face cushion comprising:
a membrane including nasal bridge, cheek and chin regions to form a continuous seal against the patient's face;
a support structure configured to connect the cushion to the frame and support the membrane, the support structure including:
a lower portion;
an upper portion extending, in at least one cross-sectional view, from the lower portion and laterally outwardly, with respect to the lower portion, the upper portion forming an angle with respect to the lower portion; and
an underlying cushion to provide support to the membrane, the underlying cushion extending from the upper portion,
wherein the membrane extends from the upper portion and covers, in a front view, the underlying cushion,
wherein an entirety of the upper portion extending between the lower portion and the membrane forms a substantially linear extension that extends laterally outwardly continuously from the lower portion to the membrane, and
wherein the angle in the nasal bridge region is different than the angle in the cheek regions of the cushion to vary a spring characteristic of the support structure in the nasal bridge region and the cheek regions of the cushion.

2. The full-face cushion according to claim 1, wherein the membrane is connected directly with the support structure and extends from the support structure, in at least one cross-sectional view, in a curved manner.

3. The full-face cushion according to claim 2, wherein the membrane delimits an opening adapted to at least partially receive the patient's nose and mouth.

4. The full-face cushion according to claim 3, wherein the membrane has a thickness that is smaller than a thickness of the support structure.

5. The full-face cushion according to claim 4, wherein the upper portion is configured to resiliently displace as a result of the cushion being positioned on the patient's face due to the spring characteristic of the support structure.

6. The full-face cushion according to claim 5, wherein a length of the upper portion varies in the different regions of the cushion.

7. The full-face cushion according to claim 6, wherein the upper portion is not part of a gusset.

8. The full-face cushion according to claim 7, wherein the lower portion is configured to connect to the frame.

9. A full-face cushion for a patient interface that delivers breathable gas to a patient, the cushion comprising different regions including nasal bridge, cheek and chin regions, the cushion being adapted to be connected to a frame, the full-face cushion comprising:
a membrane including nasal bridge, cheek and chin regions to form a continuous seal against the patient's face;
a support structure configured to connect the cushion to the frame and support the membrane, the support structure including:
a lower portion;
an upper portion extending, in at least one cross-sectional view, laterally outwardly from the lower portion, the upper portion forming an angle with respect to the lower portion; and
an underlying cushion to provide support to the membrane, the underlying cushion extending from the upper portion,
wherein the membrane extends from the upper portion and covers at least part of the underlying cushion,
wherein an entirety of the upper portion extending between the lower portion and the membrane forms a substantially linear extension that extends laterally outwardly continuously from the lower portion to the membrane,
wherein a length of the upper portion varies in the different regions of the cushion to vary a stiffness of the cushion in the different regions.

10. The full-face cushion according to claim 9, wherein the membrane is connected directly with the support structure and extends from the support structure in a curved manner.

11. The full-face cushion according to claim 10, wherein the membrane delimits an opening adapted to at least partially receive the patient's nose and mouth.

12. The full-face cushion according to claim 11, wherein the membrane has a thickness that is smaller than a thickness of the support structure.

13. The full-face cushion according to claim 12, wherein the upper portion is configured to resiliently displace as a result of the cushion being positioned on the patient's face due to a spring characteristic of the support structure.

14. The full-face cushion according to claim 13, wherein the angle in the nasal bridge region is different than the angle in the cheek regions of the cushion.

15. The full-face cushion according to claim 14, wherein the angle varies in the different regions of the cushion.

16. The full-face cushion according to claim 15, wherein the upper portion is not part of a gusset.

17. The full-face cushion according to claim 16, wherein the lower portion is configured to connect to the frame.

* * * * *